(12) United States Patent
Laughlin et al.

(10) Patent No.: US 11,564,699 B2
(45) Date of Patent: Jan. 31, 2023

(54) HANDHELD SURGICAL INSTRUMENT

(71) Applicant: MFr Technologies, Inc., Maple Grove, MN (US)

(72) Inventors: Trevor Jacob Laughlin, Minnetonka, MN (US); Jason L. Koh, Winnetka, MN (US); Daniel M. Fisher, Maple Grove, MN (US); Brian Philip Beaubien, Saint Paul, MN (US); Joseph Jude Saladino, Eden Prairie, MN (US)

(73) Assignee: MFr Technologies, Inc., Maple Grove, MN (US)

( * ) Notice: Subject to any disclaimer, the term of this patent is extended or adjusted under 35 U.S.C. 154(b) by 252 days.

(21) Appl. No.: 17/100,124

(22) Filed: Nov. 20, 2020

(65) Prior Publication Data
US 2021/0068848 A1    Mar. 11, 2021

Related U.S. Application Data

(63) Continuation of application No. 15/903,946, filed on Feb. 23, 2018, now Pat. No. 10,874,406.
(Continued)

(51) Int. Cl.
*A61B 17/80* (2006.01)
*A61B 17/16* (2006.01)
(Continued)

(52) U.S. Cl.
CPC ...... *A61B 17/1631* (2013.01); *A61B 17/1604* (2013.01); *A61B 17/1622* (2013.01);
(Continued)

(58) Field of Classification Search
CPC combination set(s) only.
See application file for complete search history.

(56) References Cited

U.S. PATENT DOCUMENTS 9,510,840 B2    12/2016  Sikora et al.
2001/0053888 A1  12/2001  Athanasiou et al.
(Continued)

FOREIGN PATENT DOCUMENTS

WO    WO 2011/ 014677    2/2011

OTHER PUBLICATIONS

Extended European Search Report from EP Application No. 18761842.6, dated Dec. 1, 2020, 10 pgs.
(Continued)

*Primary Examiner* — Sameh R Boles
(74) *Attorney, Agent, or Firm* — Patterson Thuente IP

(57) ABSTRACT

A handheld surgical instrument comprising an energy storage element, wherein the energy storage element is a spring coupled to the impacting mechanism, an impacting mechanism has a tip configured to impact a bone, wherein the tip includes a tapered point, a power transmission mechanism is configured to transmit energy from the energy storage element to the impacting mechanism, wherein the power transmission mechanism includes a semi-flexible metal wire guided by a hollow shaft, wherein the hollow shaft includes a distal end, the semi-flexible metal wire is includes a bend toward the distal end, a trigger mechanism is configured to release energy from the energy storage element, wherein the bend includes an angle between 14 degrees and 46 degrees, wherein the trigger mechanism includes a manual lever which, when actuated, simultaneously retracts the tip and charges the energy storage element.

18 Claims, 27 Drawing Sheets

Related U.S. Application Data

(60) Provisional application No. 62/596,420, filed on Dec. 8, 2017, provisional application No. 62/464,614, filed on Feb. 28, 2017.

(51) Int. Cl.
*A61B 17/00* (2006.01)
*A61B 17/92* (2006.01)

(52) U.S. Cl.
CPC . A61B 17/1637 (2013.01); *A61B 2017/00411* (2013.01); *A61B 2017/00473* (2013.01); *A61B 2017/00734* (2013.01); *A61B 2017/924* (2013.01)

(56) References Cited

U.S. PATENT DOCUMENTS

| | | |
|---|---|---|
| 2004/0147932 A1 | 7/2004 | Burkinshaw et al. |
| 2005/0065403 A1 | 7/2005 | Miller |
| 2005/0228395 A1* | 10/2005 | Auxepaules .......... A61F 2/4609 606/91 |
| 2006/0047315 A1 | 3/2006 | Colloca et al. |
| 2011/0028976 A1 | 2/2011 | Miller et al. |
| 2013/0231654 A1 | 9/2013 | Germain |
| 2013/0261681 A1 | 10/2013 | Bittenson |
| 2016/0331394 A1 | 11/2016 | Rottenberg et al. |
| 2018/0242982 A1 | 8/2018 | Laughlin et al. |

OTHER PUBLICATIONS

International Search Report and Written Opinion from PCT Application PCT/US2018/019591, dated Jun. 27, 2018, 18 pgs.

FDA Maude report 3004154314-2013-00007, "Arthrosurface Nanofx Pleuristik Guide Wire", 3 pgs, dated Oct. 26, 2015.

FDA Maude report 3004154314-2013-00009, "Arthrosurface Nanofx Pleuristik Guide Wire", 3 pgs, dated Oct. 26, 2015.

FDA Maude report 3004154314-2016-00015, "Arthrosurface, Inc. Nanofx Pleuristik GuideWire", 3 pgs, dated Dec. 16, 2016.

International Preliminary Report on Patentability from PCT Application PCT/US2018/019591 dated Sep. 12, 2019, 10 pgs.

Application and file history for U.S. Appl. No. 15/903,946, filed Feb. 23, 2020, inventors Laughlin et al.

* cited by examiner

Figure 12.
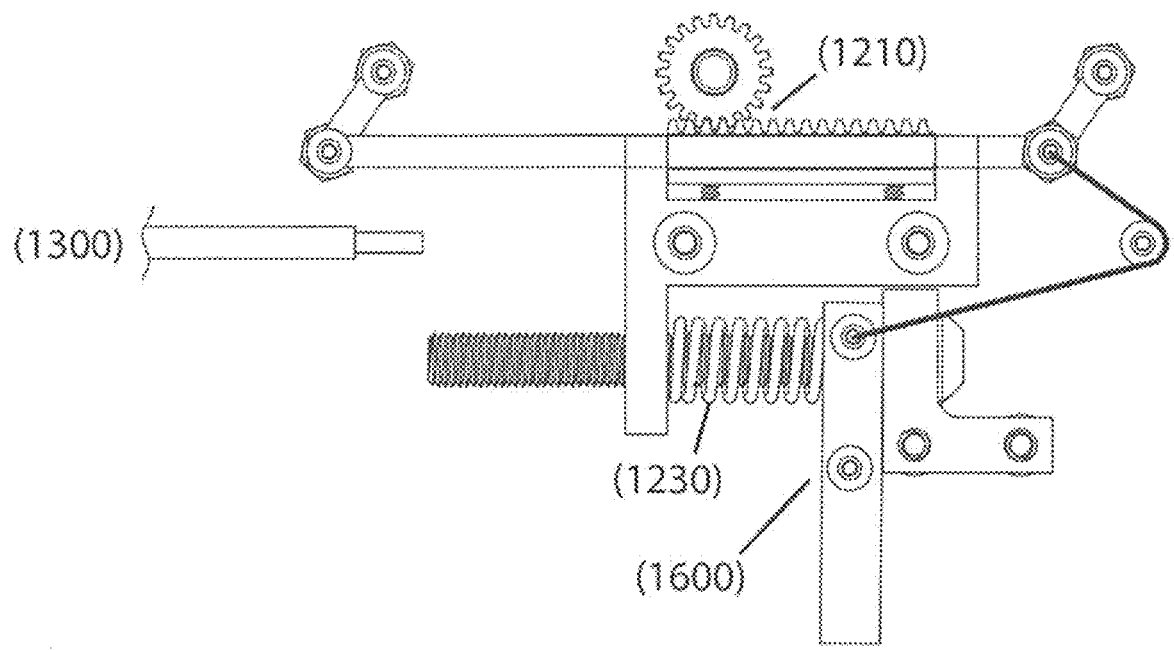
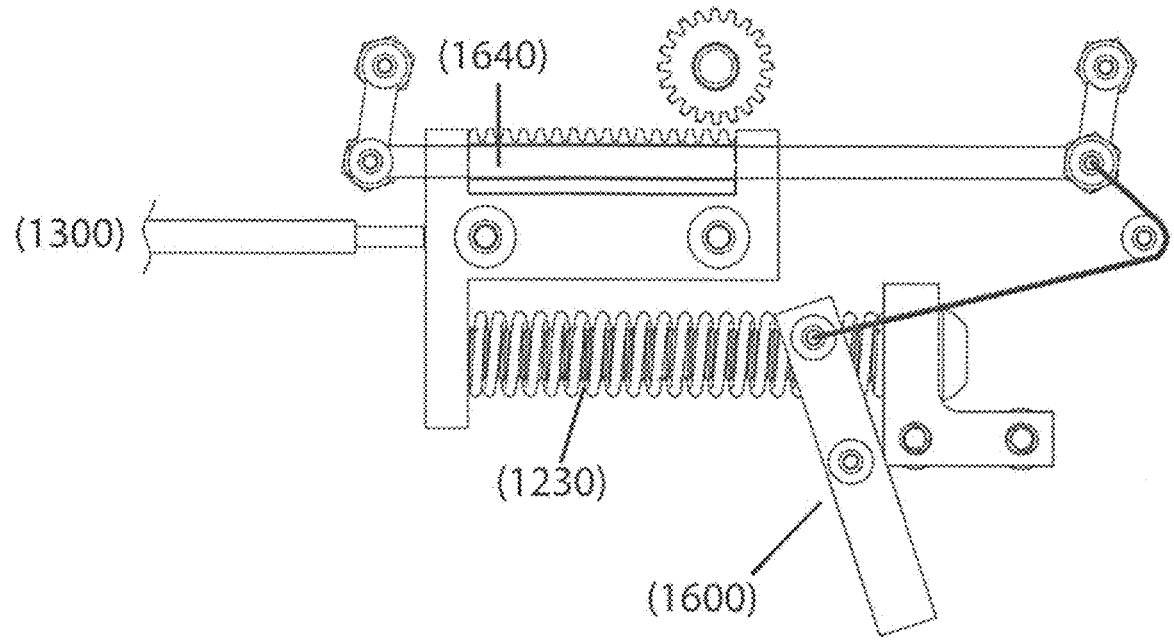

Figure 18.
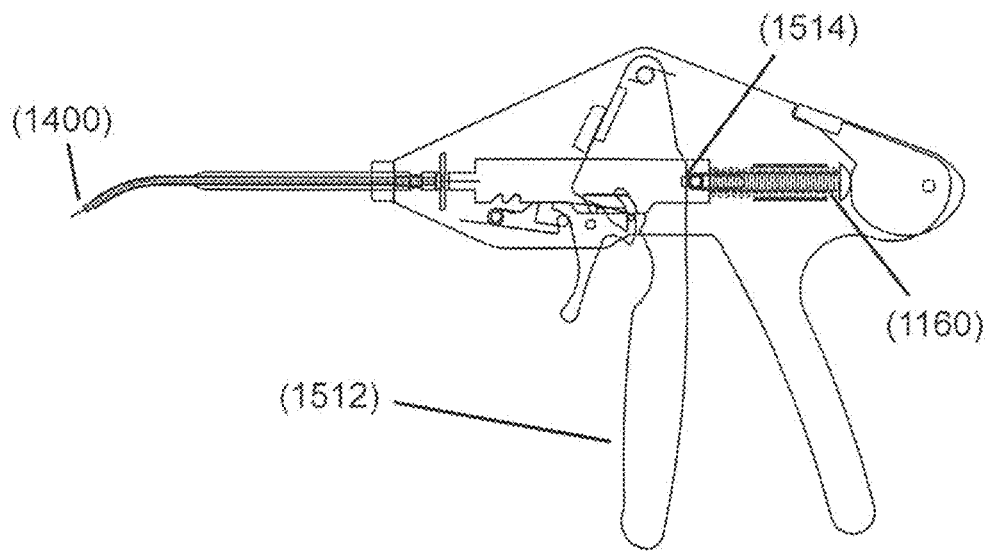
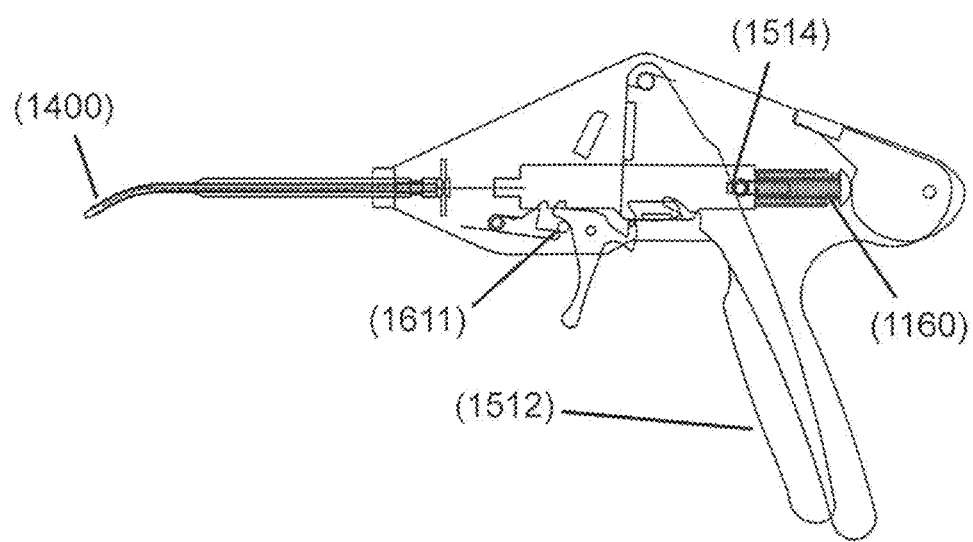
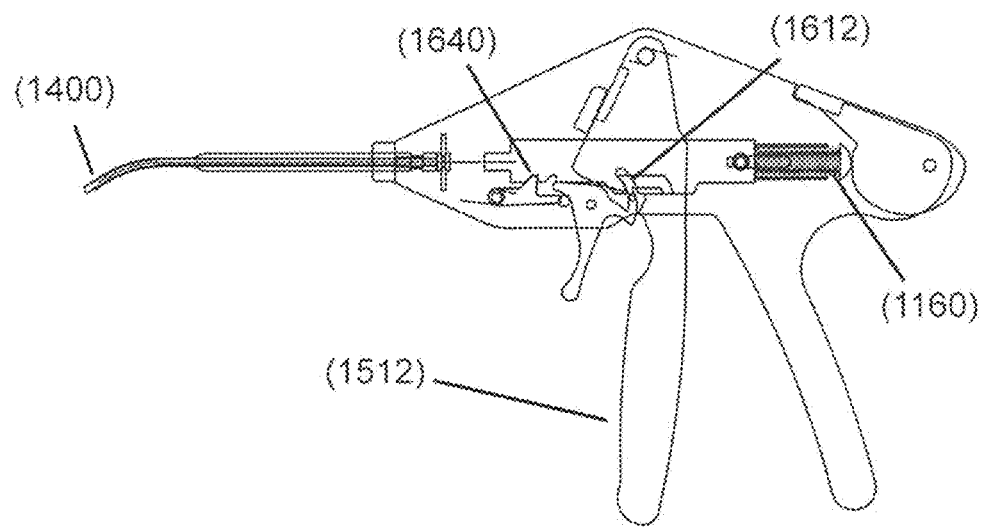

Figure 19.
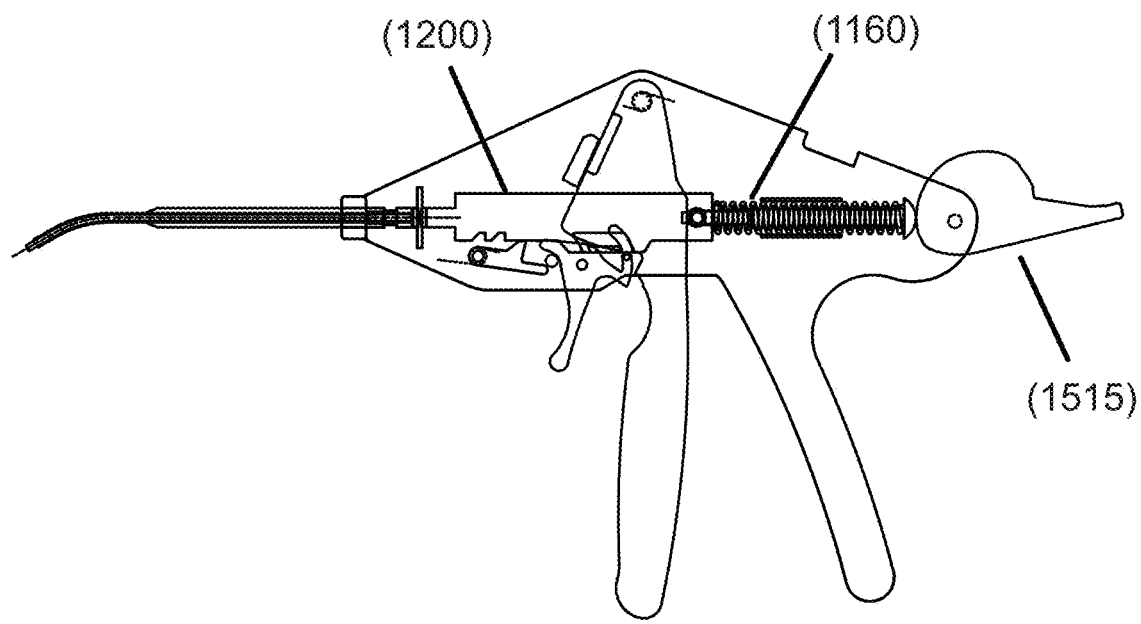
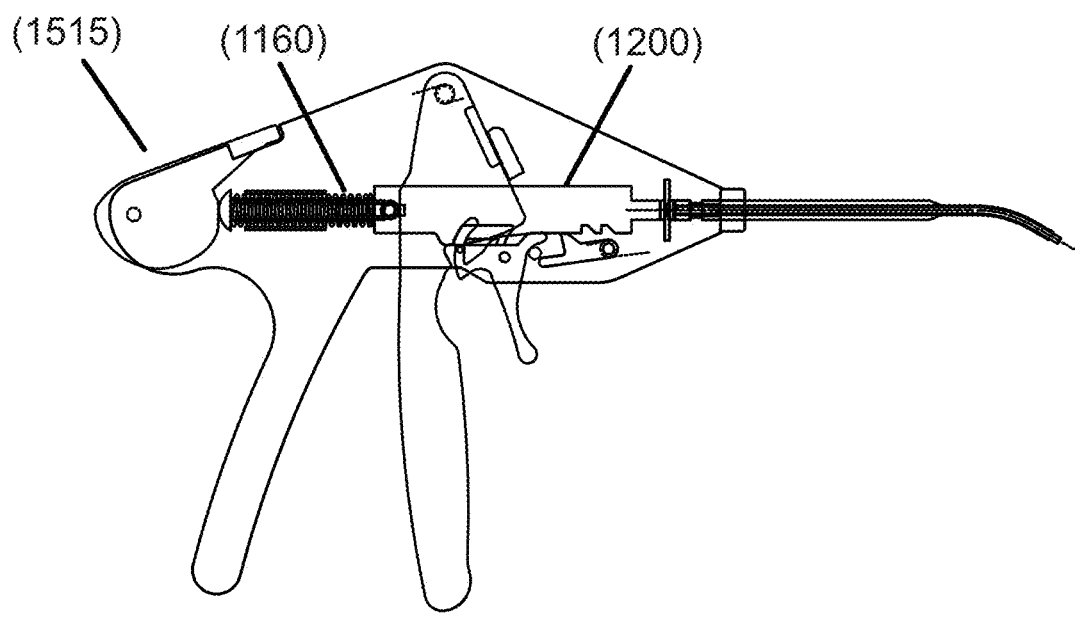

Figure 20.
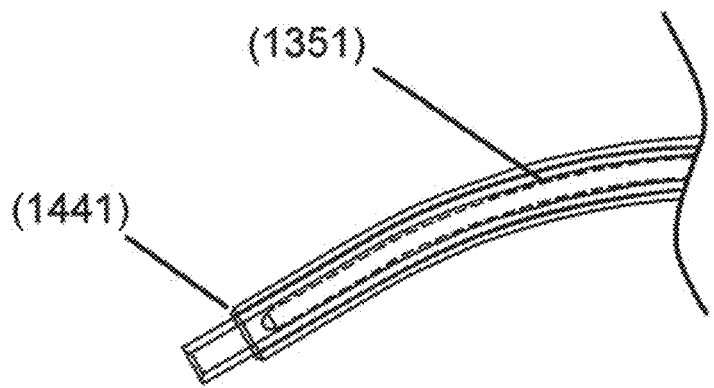
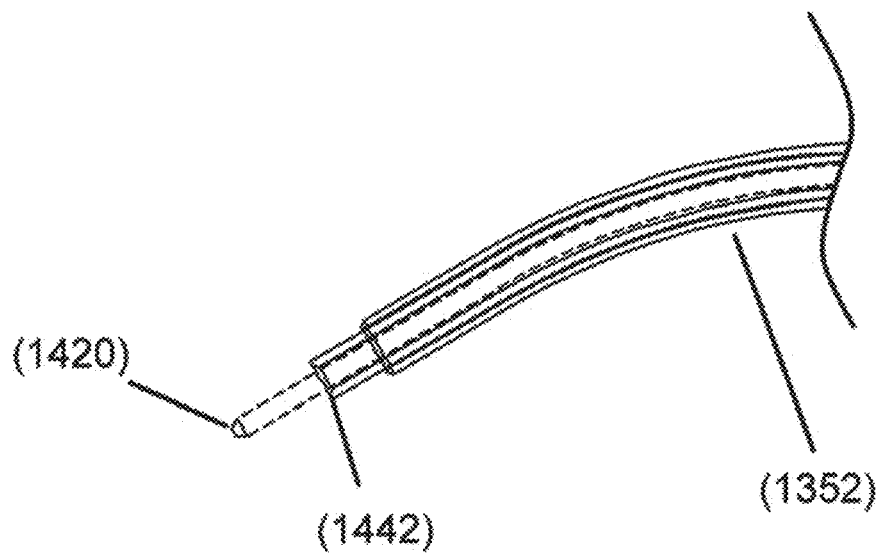
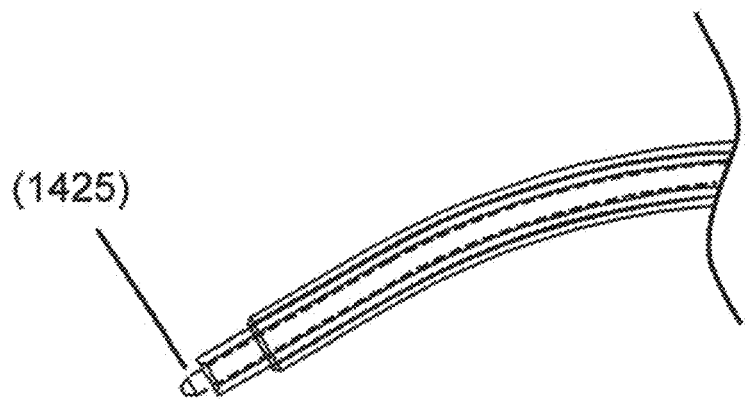

Figure 23.
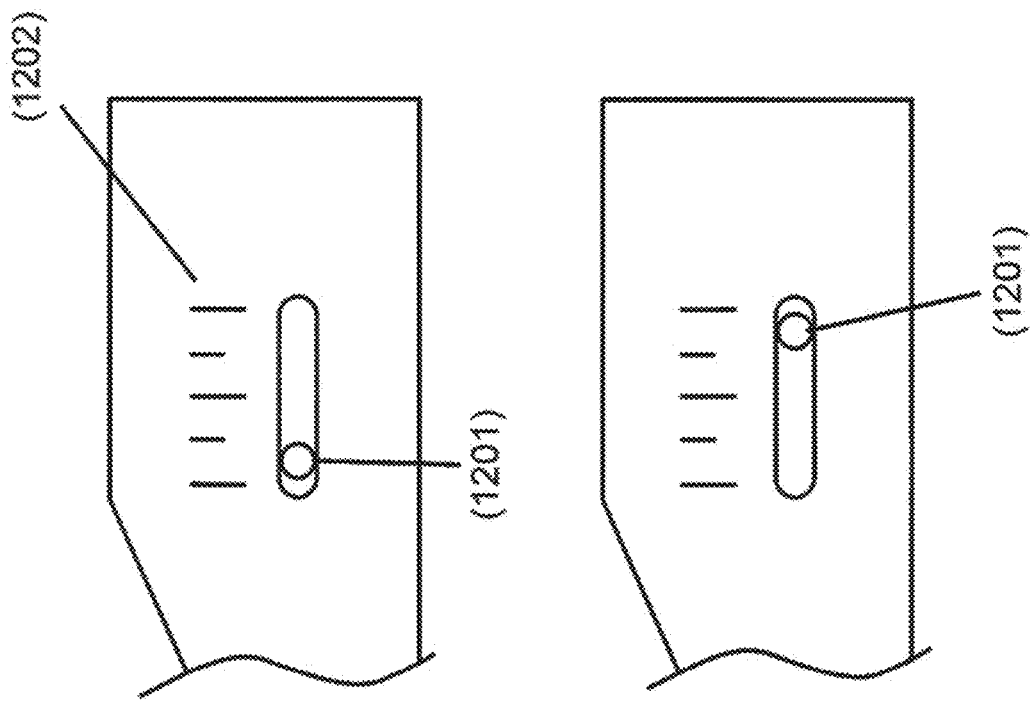
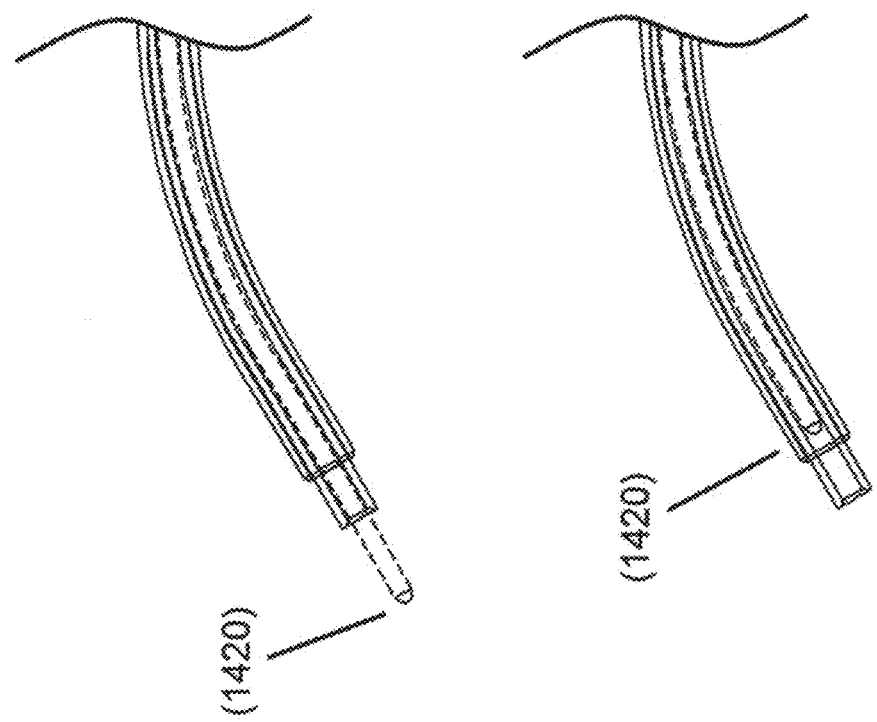

Figure 25.
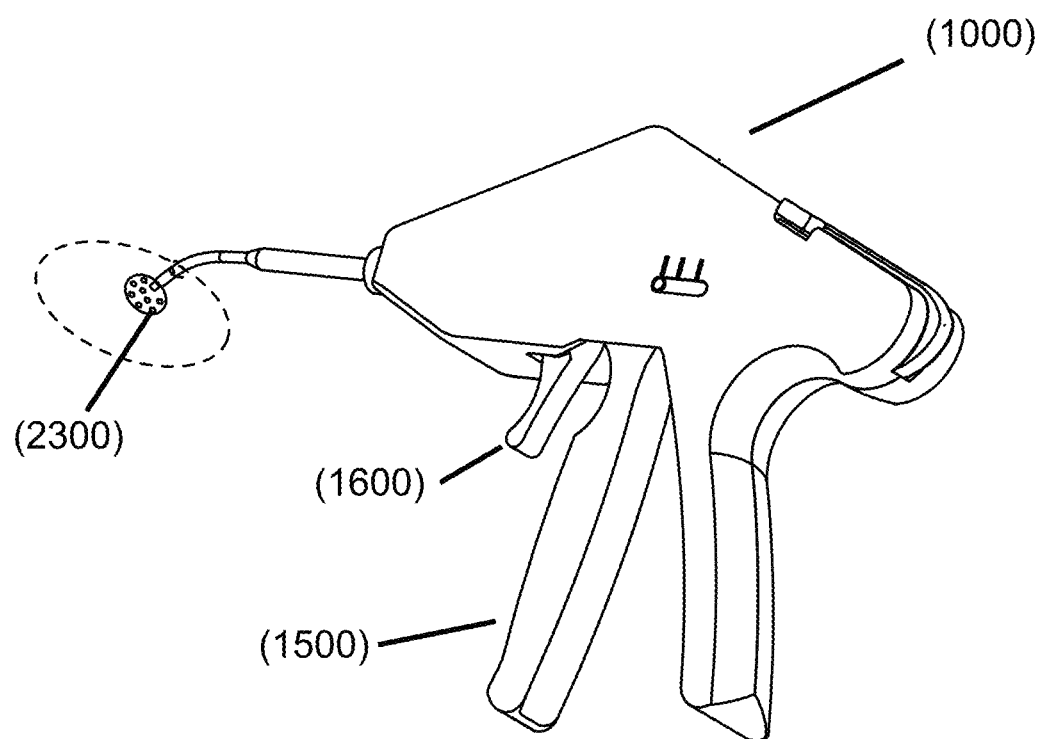
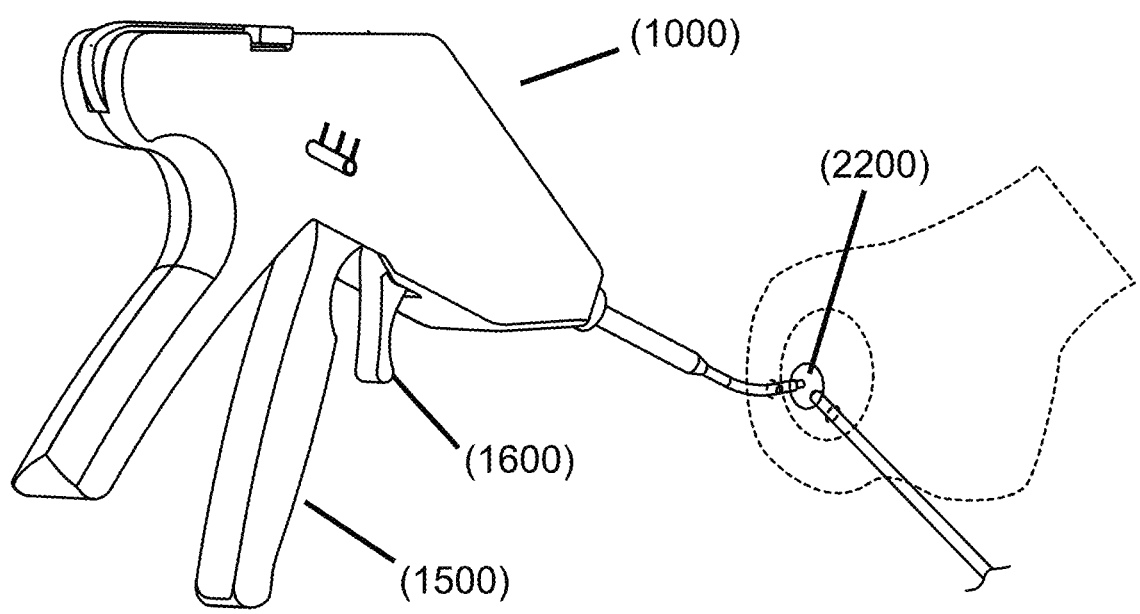

HANDHELD SURGICAL INSTRUMENT

CLAIM OF PRIORITY

This application is a Continuation of U.S. patent application Ser. No. 15/903,946, filed Feb. 23, 2018, which claims priority to U.S. Provisional Patent Application Ser. No. 62/464,614 filed Feb. 28, 2017 and U.S. Provisional Patent Application Ser. No. 62/596,420 filed Dec. 8, 2017, both of which are herein incorporated by reference.

FIELD OF THE INVENTION

The present invention is generally directed to a device for surgery, and more particularly, for accessing bone marrow for enhancement of tissue repair. One popular example use is performing automated microfracture on subchondral bone to repair articular cartilage. Other examples include the stimulation of healing in areas of tendinosis such as elbow lateral epicondylitis, patella tendinopathy, hip gluteus medius tendinopathy, and ankle achilles tendinitis; to stimulate ligament healing such as in knee medial collateral ligament sprains; to enhance soft tissue to bone healing such as in the repair of the shoulder rotator cuff tendon to bone; for the enhancement of bony healing in fractures; and in the preparation of bone for improved healing to prosthetic implants.

DESCRIPTION OF THE RELATED ART

Bone marrow and its associated cells are known to have regenerative properties which makes it valuable medicinally in areas of wear, damage, or impairment. In many cases, soft tissue and bone healing can benefit from improved access to bone marrow, typically through small holes in bone. One area of benefit is in articular cartilage repair. Articular cartilage is a smooth, low-friction tissue which covers the ends of bones and enables healthy joint function. Articular cartilage is prone to damage from excessive wear or traumatic injuries, as are common in sports. When articular cartilage is damaged, it can result in pain and reduced mobility for the patient, and in some cases subsequent arthritis. Articular cartilage has extremely limited ability to repair itself spontaneously due to absent blood flow. Microfracture surgery exists as a method to assist in the repair of articular cartilage in order to improve joint function. Microfracture creates a pathway for cartilage-building cells in blood and bone marrow to travel from the underlying cancellous bone to the articular surface by producing small holes in the cortical bone. Microfracture procedures are typically performed using an awl or a pick that is hit with a hammer.

Other conditions where healing is often limited or impaired occurs in degenerative conditions where soft tissue attaches to bone, such as in rotator cuff tears and various insertional tendinopathies such as elbow lateral epicondylitis, patella tendinopathy, and Achilles tendinitis. In these situations, there is again limited or absent blood flow, and therefore healing is impaired without access to the necessary cells and growth factors. Drilling or perforation of the bone is performed to allow bone marrow and blood to access the area of damage. Similarly, in cases of delayed or absent fracture healing, or in the preparation of surfaces for bone to implant healing, drill holes are often made to allow bone marrow and blood to reach the area of relatively poor circulation.

Some marrow access devices, for example U.S. Pat. No. 9,510,840 ("the '840 patent), are utilized via driving a wire with a hammer through an angled cannula. Like the hammer and awl method, this method requires a minimum of three hands to operate, and delivers inconsistent results due to its subjective and uncontrolled external force delivery, which is a problem in microfracture procedures. Furthermore, the awl-like design and its associated user experience of applying aggressive, torsional, radial and axial force to remove the tip can result in tips breaking as documented in FDA MAUDE reports 3004154314-2013-00007, 3004154314-2013-00009, 3004154314-2016-00015, and several others, which are incorporated by reference. While a removal tab is claimed in the '840 patent, insufficient mechanical advantage and poor user experience design leads operators to resort to excessive lateral and axial force, such as hitting the tab with a hammer and/or aggressively shimmying it back and forth, delivering treacherous stresses to the bone plate and the penetrator, weakening both and compacting the sides of the channel.

Some automated microfracture devices have been introduced which rely on external power sources such as compressed air or specialty electrical power supplies. This presents a challenge as many surgical facilities are without access to said power sources.

SUMMARY

Reported clinical results of microfracture are very good in some cases, but other researchers have reported relatively poorer results. Part of this may be related to the variability of the manually performed technique. To improve effectiveness during procedures, active surgeon feedback such as good visibility is of prime importance. Many marrow access procedures are performed arthroscopically. Operating a surgical scope (arthroscope) requires focus, precision, and a steady hand, and the coordination of meticulous hole creation relies upon such control. Therefore the primary operator is often inclined to maintain control of the scope. This leaves the primary operator's other hand available for one of two tasks: Hold the awl, or swing the hammer. Both of these require equal or higher levels of finesse to operate effectively, and are interdependent from one another and from the scope.

To date, the typical method of performing microfracture involves holding a longitudinal awl with an angled tip, and a hammer for impacting the proximal end of the handle of said awl. At the same time, a surgical scope must be held and positioned in a manner which allows the surgeon to see the tip alignment, the depth of penetration, and the subsequent blood flow from each hole produced. As such, a problem exists in that at least three hands are required to perform such a procedure using the historically accepted method. While each tool must be operated with careful precision, and the feedback from each tool is interdependent, coordinating a microfracture procedure with a minimum of two operators presents a challenge.

There are several technical challenges associated with the creation of microfracture holes in the bone. The depth of penetration must be sufficient to adequately access the bone marrow elements underneath the relatively avascular subchondral bone. The holes must be of sufficient width to allow bone marrow and blood to reach the surface of the bone, while not being so large as to significantly affect the load-bearing characteristics of the bone. Holes must be adequately spaced apart to allow for adequate flow to cover the surface, but not collapse into each other. Ideally, the holes should be perpendicular to the surface so that minimal tissue is perforated to allow access to the bone surface.

The standard technique uses a hammer manually impacting the back end of the awl. This can result in a highly variable amount of force being applied, resulting in unpredictable hole size and depth. In addition, excessive load can cause significant bone edema, pain and loss of function in patients.

Furthermore, the direction of force applied by the hammer is not substantially aligned with the orientation of the tip, and the tip may not be perpendicular to the bone surface. This often results in substantial undesired damage to the subchondral bone, since an oblique hole or trough may be created. In many cases, the lateral force transmitted to the awl tip causes the tip to break into an adjacent hole, significantly disrupting the subchondral bone. In other cases, the individual holes created may be much wider than what is necessary, leading to complications and prolonged recovery time.

There are also multiple awl types, sizes, and tip designs. Many of these designs have very thick and robust tips to withstand the obliquely applied hammering force, but this can create issues with size of hole creation. In addition, the majority of these instruments are multiple-use, and tend to dull or blunt over time, resulting in a need for increased force application to create the holes.

Another example application of the present invention is to improve access to bone marrow and blood to enhance soft tissue or bony healing, including fracture union, fusion, or healing to prosthetic implants. Insufficient access to bone marrow in said procedures can result in reduced progenitor cells and growth factors, and ultimately substandard clinical outcomes. Currently, this access is achieved either with the use of an awl, with the previously described deficiencies; or by drilling into the bone. Drilling of the bone has several limitations: typically, this is performed through an open and not minimally invasive surgical technique. The angle of drilling is usually limited by use of a straight drill bit. Larger holes can weaken the underlying bony tissue, while smaller drill bits are prone to breakage due to the often awkward positioning and unbalanced size of the power drill. Drilling has also been implicated in thermal necrosis (death) of the bone, which is counterproductive in the healing environment. This can be exacerbated by the typical reuse of many drill bits which become duller with continued use. Finally, drilling with the typical size drill and bit is usually a two handed procedure requiring an assistant to retract adjacent tissue.

The present invention introduces a novel instrument for use in microfracture procedures and other bone marrow access procedures which solves the multiple issues mentioned above. The novel instrument can be operated using one hand, emulating both the hammer and the awl of the historically accepted microfracture procedure, or the stabilized drill and bit. In such form, one operator may coordinate each essential surgical element simultaneously with precision. Additionally, the device can have variable angles to access the bone, unlike a straight awl or drill bit. The present invention demonstrates a means of transmitting power to a force in a direction better aligned with the orientation of the tip. This device can deliver a precise load and direction to the tip, resulting in much better controlled hole size, shape, and depth. Another advantage is a disposable tip, which can also increase the average sharpness of the instrument when used.

The present invention comprises a one-handed solution for creating holes in tissue. The instrument comprises six main parts, including a master energy storage element (1100); an impact mechanism (1200); a power transmission mechanism (1300); a tip (1400); a means of energy input (1500); and a trigger mechanism (1600). Two or more of these parts may be combined, for example in a direct drive configuration, whereby the impact mechanism, the power transmission mechanism, and the tip are all connected.

In one embodiment of the present invention, the handheld surgical instrument (1000) comprises a flat spring (1150) as a master energy storage element (1100); an impacting drive mechanism utilizing a linear spring (1230); a power transmission mechanism (1300); an elongated shaft comprising a distal end and a proximal end, and angled at 30 degrees; a tip with a proximal end (1410), which may be engaged by the power transmission mechanism and a distal end (1420) with a sharpened point (1421) for engaging the subchondral bone; a means of energy input by the user (1500); and a trigger mechanism (1600) to initiate impact.

In another embodiment of the present invention, the handheld surgical instrument (1000) comprises a compressed fluid cylinder (1110) as the master energy storage element (1100); an impacting drive mechanism (1200) powered directly by the master energy storage element (1240); a power transmission mechanism (1300); an elongated shaft comprising a distal end and a proximal end, and angled at 90 degrees; a tip (1400) with a proximal end (1410), which may be engaged by the power transmission mechanism (1411) and a distal end (1420) with a drill point (1423) for engaging the subchondral bone; a means of energy input by the user (1500); and a trigger mechanism (1600) to initiate impact.

In another embodiment of the present invention, the handheld surgical instrument (1000) houses a direct-drive carriage, which is connected to the power transmission mechanism (1300) and to the tip (1400), together forming the impact mechanism (1200). In this embodiment, the proximal end of the tip and the semi-flexible wire within the bent shaft, that is the power transmission mechanism, are one in the same.

In one embodiment of the present invention, the entire device is disposable, so as to ensure a safe and sterile procedure administered by the device. In another embodiment, the tip is removable, and can be cleaned by standard reprocessing methods.

In yet another embodiment, the present invention includes a handheld surgical instrument having an energy storage element, wherein the energy storage element is a spring coupled to the impacting mechanism, the impacting mechanism having a tip configured to impact a bone, wherein the tip includes a tapered point, a power transmission mechanism is configured to transmit energy from the energy storage element to the impacting mechanism, wherein the power transmission mechanism includes a semi-flexible metal wire guided by a hollow shaft, wherein the hollow shaft includes a distal end, wherein the semi-flexible metal wire is includes a bend toward the distal end. A trigger mechanism is configured to release energy from the energy storage element, wherein the bend includes an angle between 14 degrees and 46 degrees, wherein the trigger mechanism includes a manual lever which, when actuated, simultaneously retracts the tip and charges the energy storage element.

In an alternative embodiment, the invention includes a method of performing surgery that includes the use of a handheld surgical instrument comprising an energy storage element, wherein the energy storage element is a spring coupled to the impacting mechanism. An impacting mechanism has a tip configured to impact a bone, wherein the tip includes a tapered point. A power transmission mechanism is configured to transmit energy from the energy storage element to the impacting mechanism, wherein the power transmission mechanism includes a semi-flexible metal wire guided by a hollow shaft, wherein the hollow shaft includes a distal end. The semi-flexible metal wire is includes a bend toward the distal end. A trigger mechanism is configured to release energy from the energy storage element, wherein the bend includes an angle between 14 degrees and 46 degrees, wherein the trigger mechanism includes a manual lever which, when actuated, simultaneously retracts the tip and charges the energy storage element.

These and various other characteristics are pointed out with particularity in the claims annexed hereto and form a part hereof. Reference should also be made to the drawings which form a further part hereof, and to accompanying descriptive matter, in which there are illustrated and described representative examples of systems, apparatuses, and methods.

BRIEF DESCRIPTION OF THE DRAWINGS

The elements and workings of the present invention can be better understood by taking into account the underlying detailed description of the invention in conjunction with the definitions listed below. Elements are labeled numerically and hierarchically to help the reader better understand individual references and their inherent relationships. Like numbers refer to like parts and furthermore;

(1XXX.) refers to any part or feature of the instrument;
(11XX.) refers to any part or feature of the instrument relating directly to the master energy storage element;
(12XX.) refers to any part or feature of the instrument relating directly to the impact mechanism;
(13XX.) refers to any part or feature of the instrument relating directly to the power transmission mechanism;
(14XX.) refers to any part or feature of the instrument relating directly to the tip;
(15XX.) refers to any part or feature of the instrument relating directly to the means of energy input;
(16XX.) refers to any part or feature of the instrument relating directly to the trigger mechanism.
(2XXX.) refers to anatomical structures in microfracture procedures;
(21XX.) refers to cartilage tissue;
(22XX.) refers to subchondral bone tissue;
(23XX.) refers to openings created by microfracture procedures;
(24XX.) refers to cancellous bone;
(3XXX.) refers to the orientation and the direction of force applied to the tip;
(31XX.) refers to the tip geometry which interacts with the tissue;
(32XX.) refers to the angle of the tip with respect to the surface of the subchondral bone plate.

FIG. 12 is an assembled view of one possible embodiment of the Impact Mechanism (1200).
FIG. 18 illustrates possible retraction and charging or energy input of the Device (1000).
FIG. 19 illustrates an example of optional secondary Energy Input Mechanism (1500).
FIG. 20 illustrates an example of the Tip (1400) interacting with the Power Transmission Mechanism (1300).
FIG. 23 illustrates an example embodiment of the depth indicator.
FIG. 25 illustrates an example of the Device in use on a patient in an open and in an arthroscopic procedure.

In the figures, like reference numerals designate like elements.

DETAILED DESCRIPTION

Figure 1:
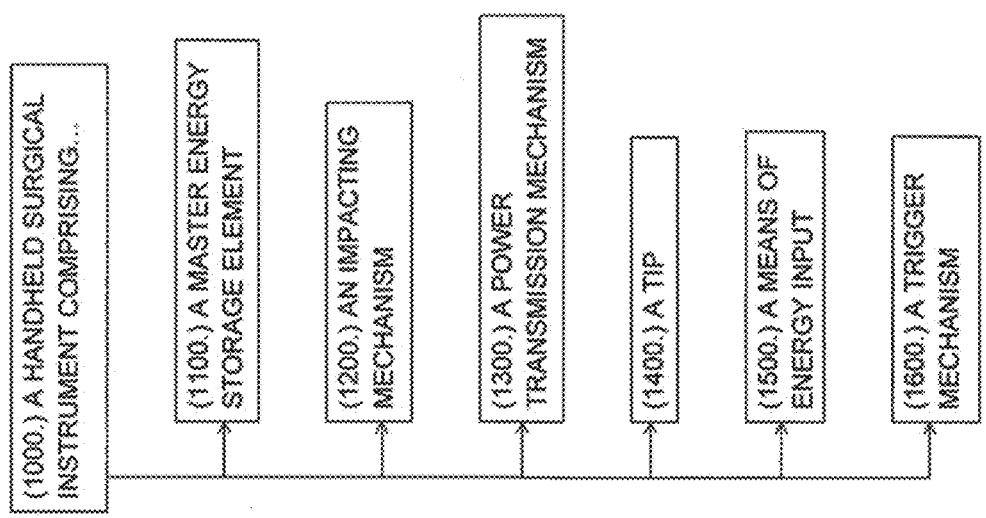
FIG. 1 is a block diagram of the Device (1000).
Figure 2:
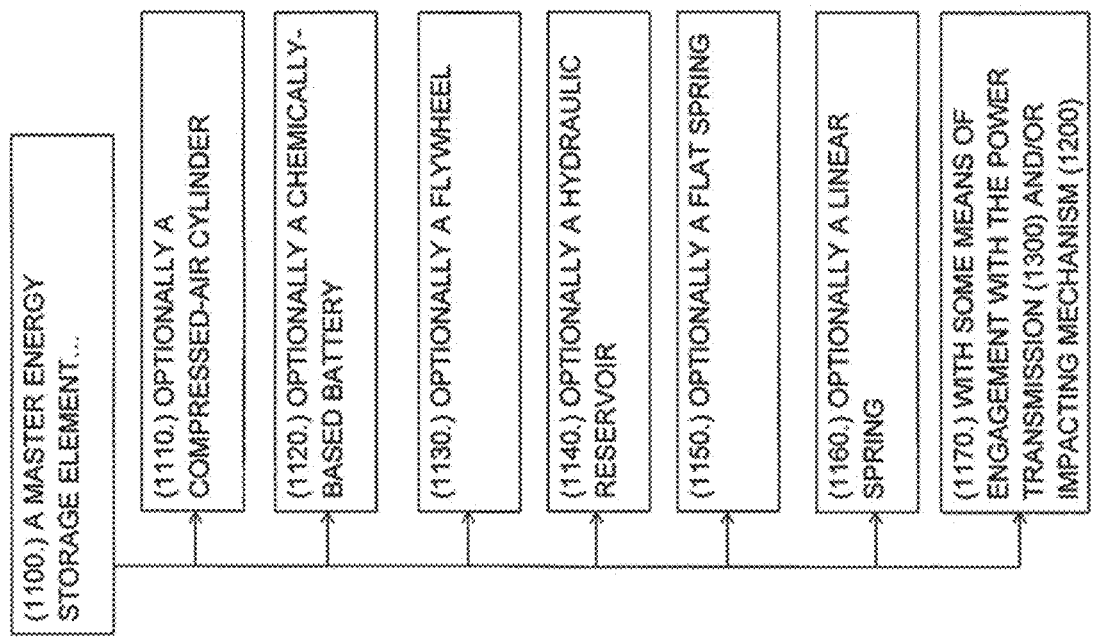
FIG. 2 is a block diagram of the Master Energy Storage Element (1100).
Figure 3:
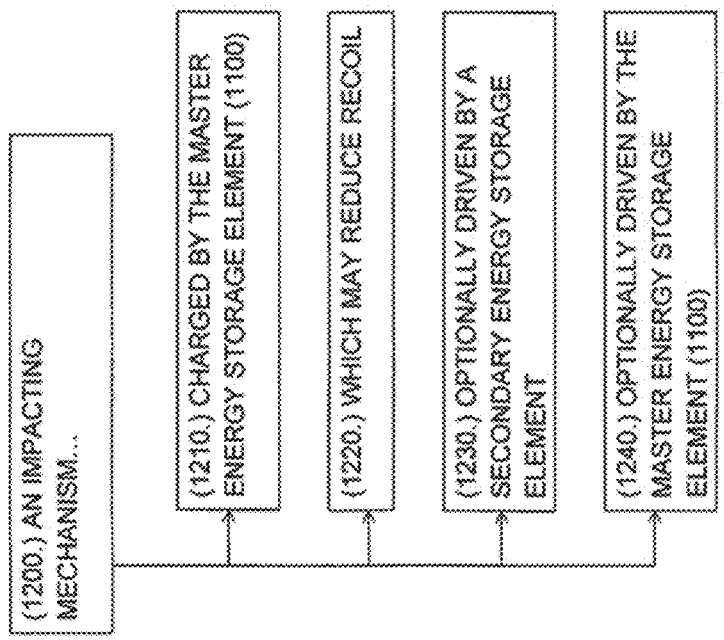
FIG. 3 is a block diagram of the Impact Mechanism (1200).
Figure 4:
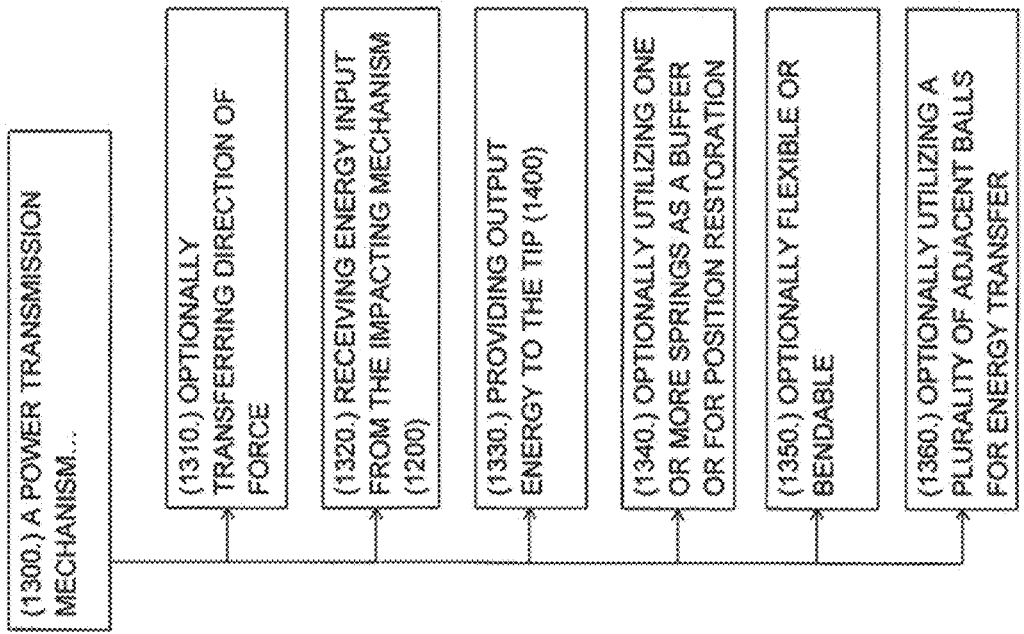
FIG. 4 is a block diagram of the Power Transmission Mechanism (1300).
Figure 5:
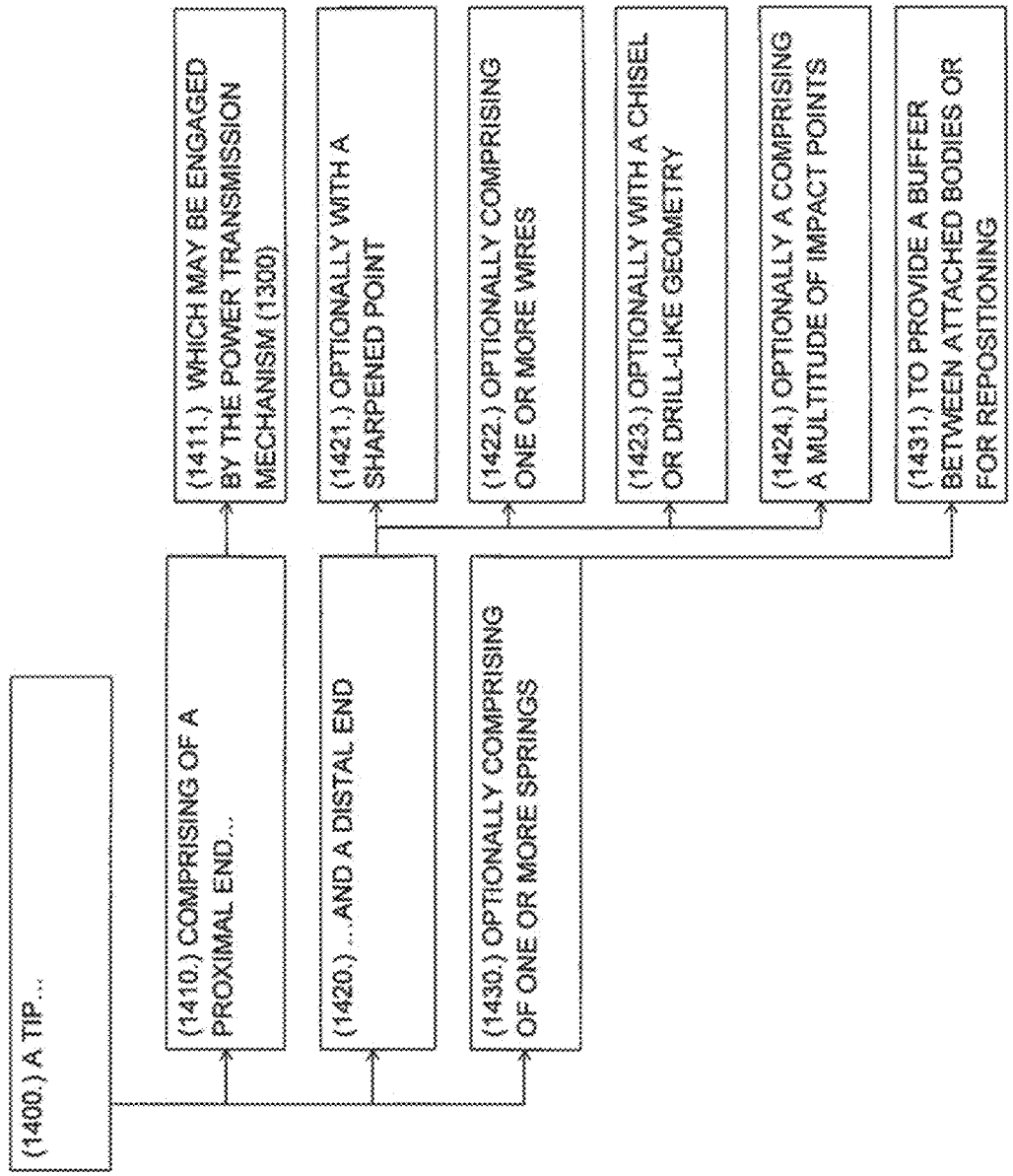
FIG. 5 is a block diagram of the Tip (1400).
Figure 6:
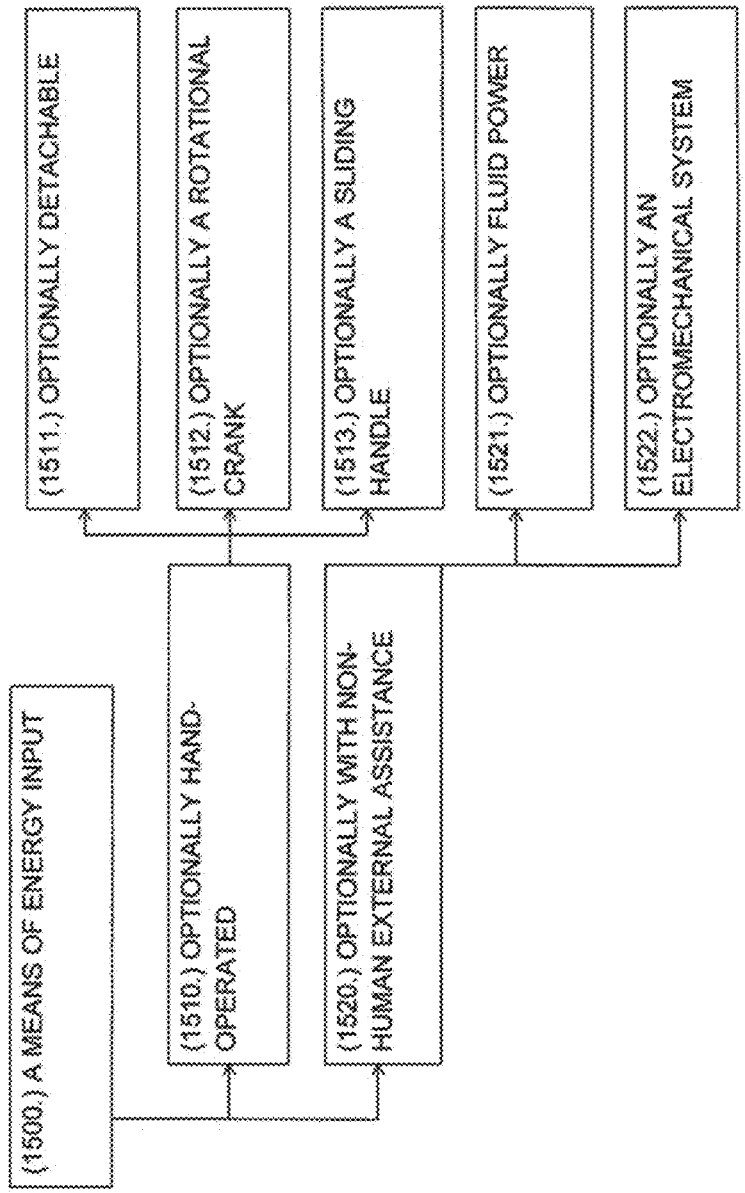
FIG. 6 is a block diagram of the Means of Energy Input (1500).
Figure 7:
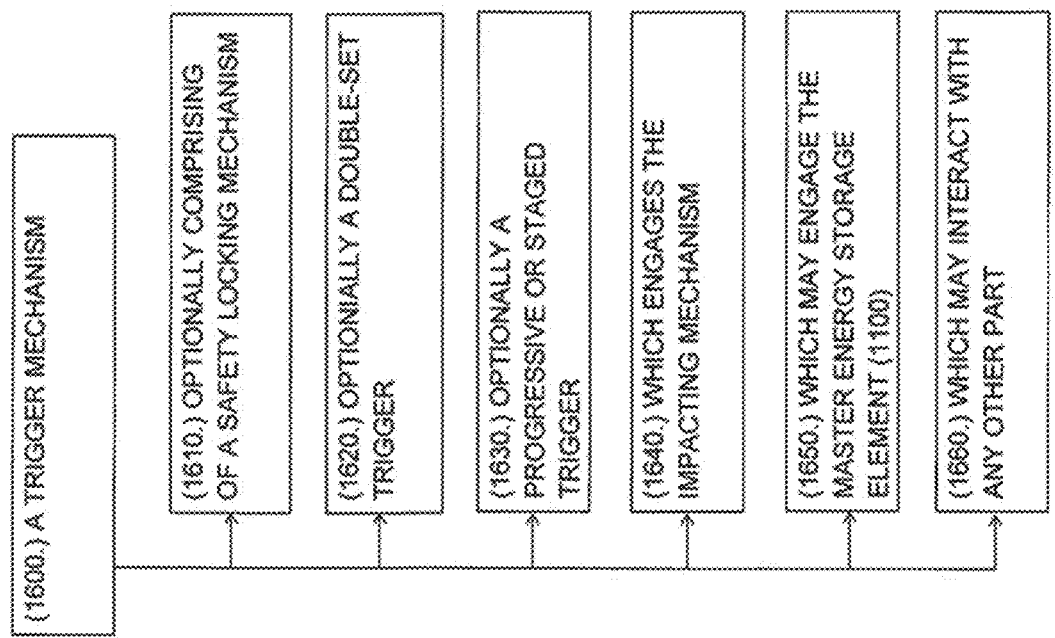
FIG. 7 is a block diagram of the Trigger (1600).

In the following description, reference is made to the accompanying drawings that form a part hereof, and in which is shown by way of illustration various embodiments in which the invention may be practiced. It is to be understood that other embodiments may be utilized, as structural and operational changes may be made without departing from the scope of the present invention. The following detailed description, therefore, is not to be taken in a limiting sense, and the scope of the invention is defined by the appended claims.

The present invention comprises a handheld surgical instrument for creating holes in tissue. The instrument comprises six main parts, including a master energy storage element (1100); an impact mechanism (1200); a power transmission mechanism (1300); a tip (1400); a means of energy input (1500); and a trigger mechanism (1600).

In one embodiment, the master energy storage element (1100) is a flat coil spring wound around two cylinders, one cylinder being the "storage drum", and the other being the "output drum". By way of example and not limitation, this flat spring could be Vulcan Spring SV12J192. When assembled in an arrangement where the center of the output drum is fixed at a particular distance from the center of the storage drum—2.60 inches in this case—the winding of the spring around the two drums can result in a torque curve that is nearly constant as the spring length travels from the output drum to the storage drum. The flat coil spring in this assembly shall be referred to as a "constant torque spring". In this example, the resulting torque is approximately 7.50 in-lbs. This resulting torque can be applied to various mechanisms within the device. In one embodiment, the output drum is fixed to a shaft which is also attached to a ratcheting mechanism. By way of example and not limitation, the means of energy input (1500) could be achieved through a sliding handle which the user may operate to engage the ratcheting gear, rotating the output shaft, transferring the length of the flat coil spring to the output drum and "charging" the constant torque spring master energy storage element. In one embodiment, the torque from the flat spring is used to charge the impact mechanism (1200) with a rack and pinion arrangement. The ratcheting pawl may be disengaged from the ratcheting gear by a user-operated lever, freeing the constant torque spring to do work. By way of example and not limitation, the pinion gear, a 14.5 degree pressure angle, 20 tooth spur gear with a 0.625 inch pitch diameter (McMaster 6867K553), is fixed to a shaft which is also fixed to the output drum. In this example, the pinion may engage with a fitting rack in order to compress a linear compression spring. By way of example and not limitation, the linear compression spring could be a 2.50 inch long stainless steel spring with a spring constant of 16.90 lbs/inch which compresses to 1.33 inches (McMaster 1986K19). In this example, the linear spring produces 19.773 lbs of force when fully compressed. With the specified constant torque spring and the specified pinion gear in this example, a total force of 24 lbs can be applied to the rack and subsequently, the linear compression spring—enough to fully compress said spring. In this example, the rack has a slot which is used constrain it to sliding only, whereas the coupler of a parallel four bar mechanism is mated with the slot, and can be used to change the height of the slot with respect to the pinion, engaging or disengaging the rack with the pinion. In this example, the trigger (1600) is attached to the parallel four bar mechanism. Once the linear compression spring is fully compressed, the trigger can be used to disengage the rack from the pinion gear, "firing" a metal carriage which acts as an impacting mass for energy transfer. The impacting mass engages the power transmission mechanism (1300). By way of example and not limitation, the power transmission mechanism may consist of a stainless steel rod inside a stainless steel shaft on one side, and a plurality of tightly toleranced stainless steel balls, as a clearance fit, inside the other end of the shaft, which is optionally bent. In this example the rod is held flush against the balls by an extension spring mated to the rod and when the impacting mass impacts the rod, energy is transferred through the balls to the tip, conserving momentum and providing output energy to the tip (1400). By way of example and not limitation, the tip may include a sharpened metal body with a blunt proximal end for engaging the distalmost stainless steel ball of the power transmission mechanism. In this example the tip is constrained axially to the shaft but not rigidly fixed to said shaft. In this example, a small light compression spring is used as a buffer between the sharpened body and the shaft so that the majority of energy from the impacting drive mechanism may be applied to the sharpened tip body without the additional inertia of the shaft. The result is that the sharpened tip may engage the subchondral bone with majority axial force, driving to a sufficient depth and not producing any unnecessary damage to the subchondral bone.

Figure 8:
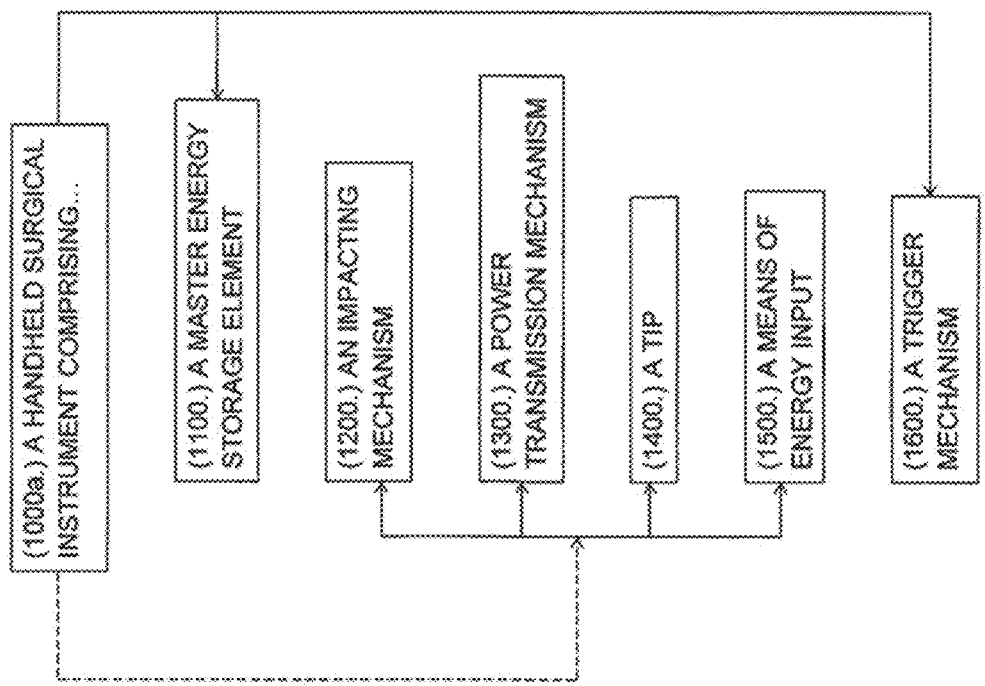
FIG. 8 is a block diagram of the Device in an alternate embodiment (1000a).
Figure 9:
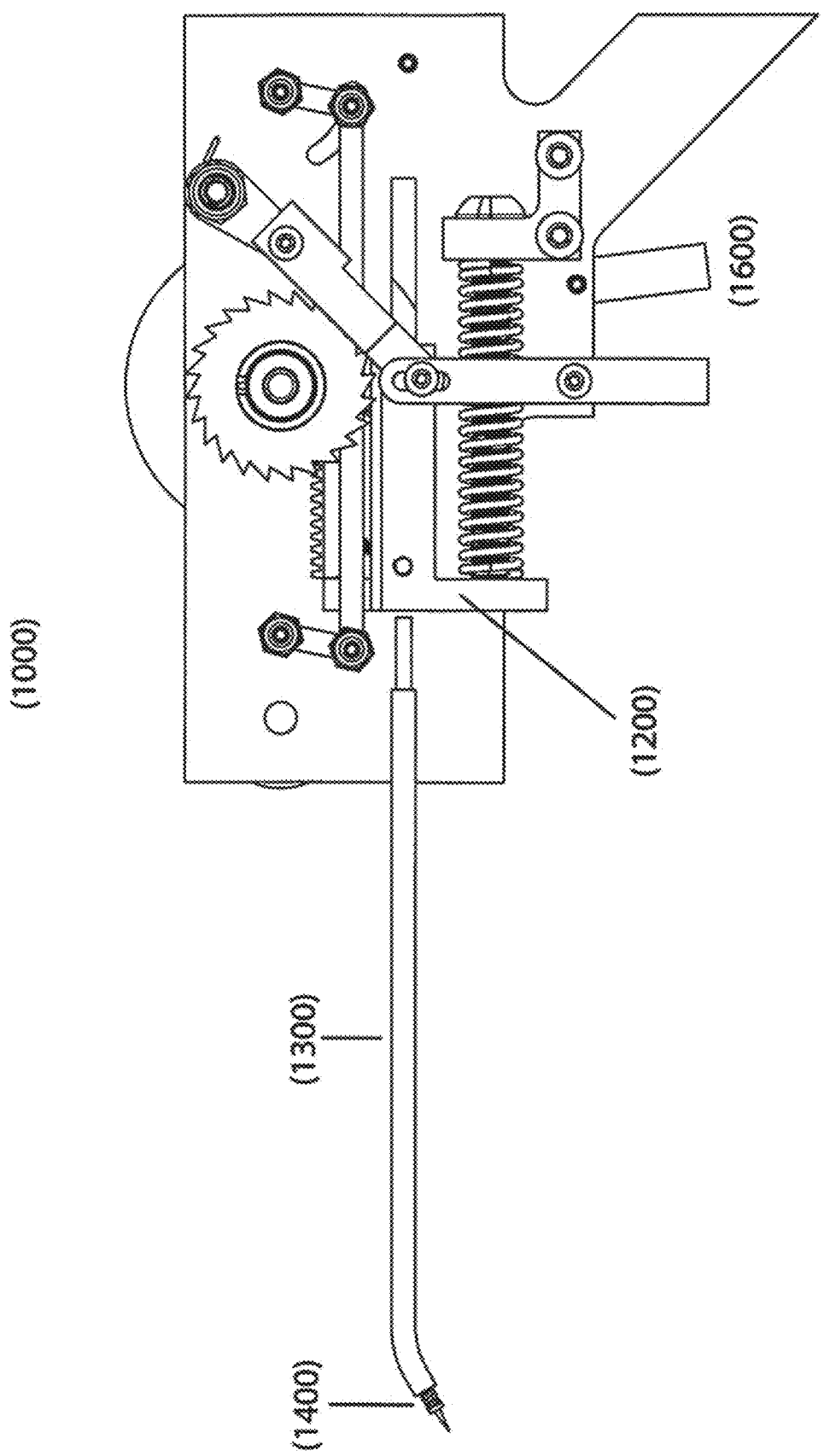
FIG. 9 is an assembled view of one possible embodiment of the Device (1000).
Figure 10:
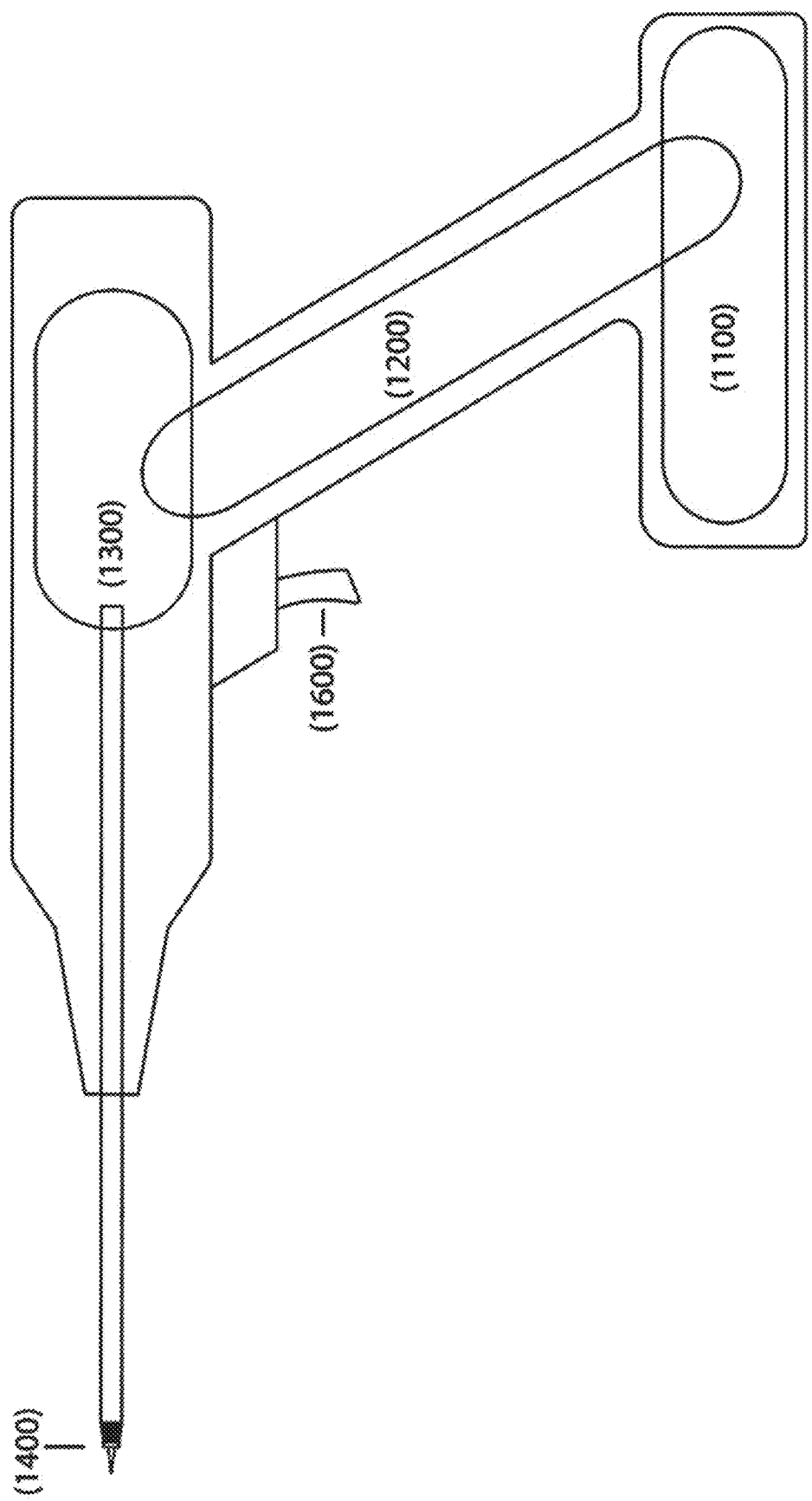
FIG. 10 is a representation of an alternate embodiment of the Device (1000).
Figure 11:
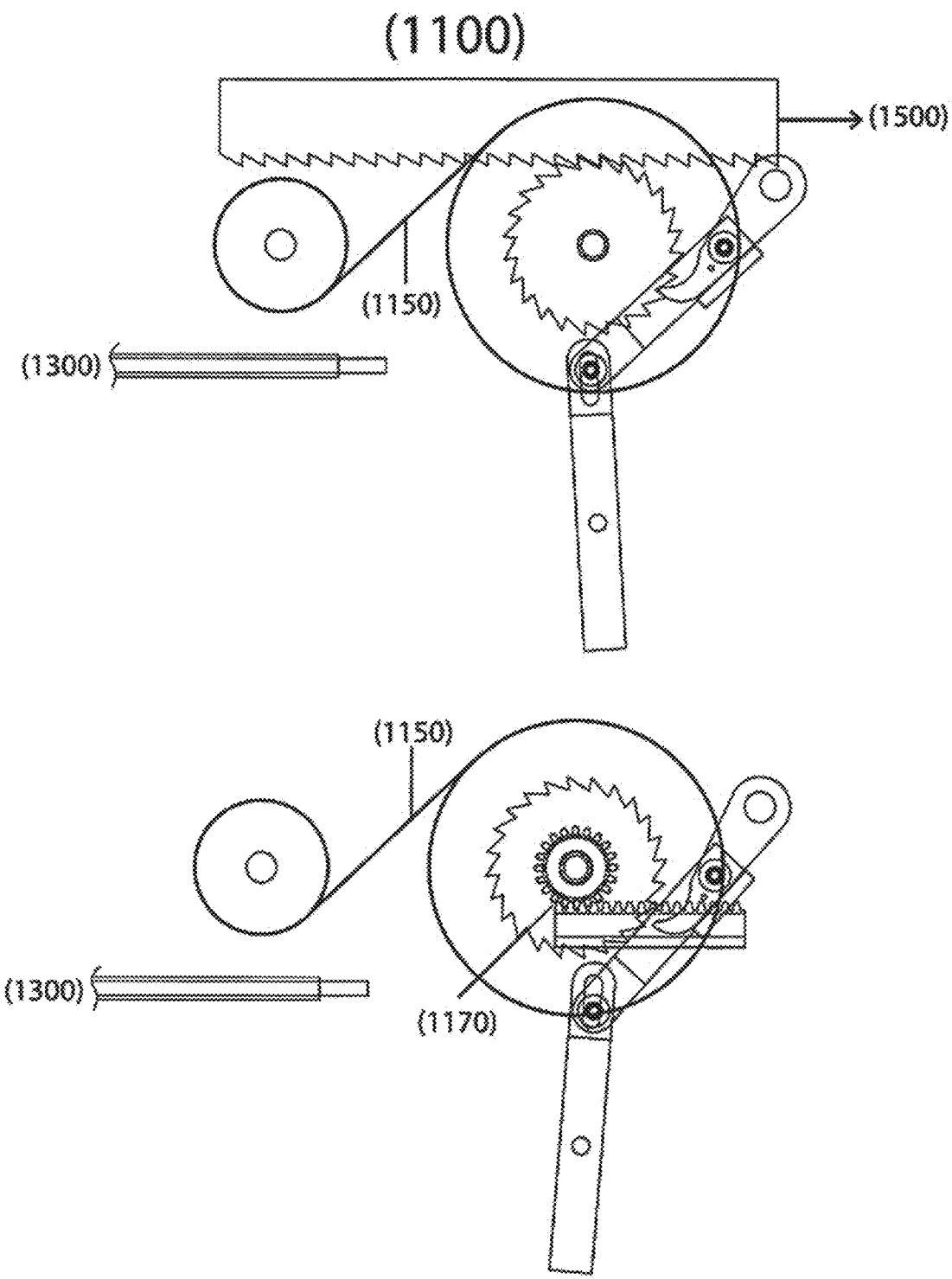
FIG. 11 is an assembled view of one possible embodiment of the Master Energy Storage Element (1100).
Figure 13:
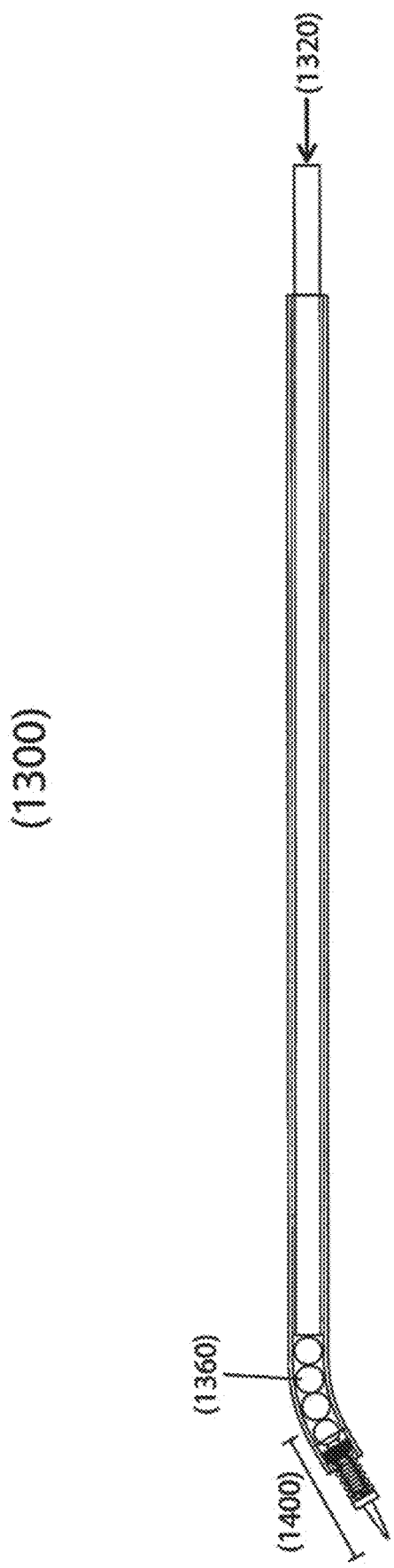
FIG. 13 is an assembled view of one possible embodiment of the Power Transmission Mechanism (1300).
Figure 14:
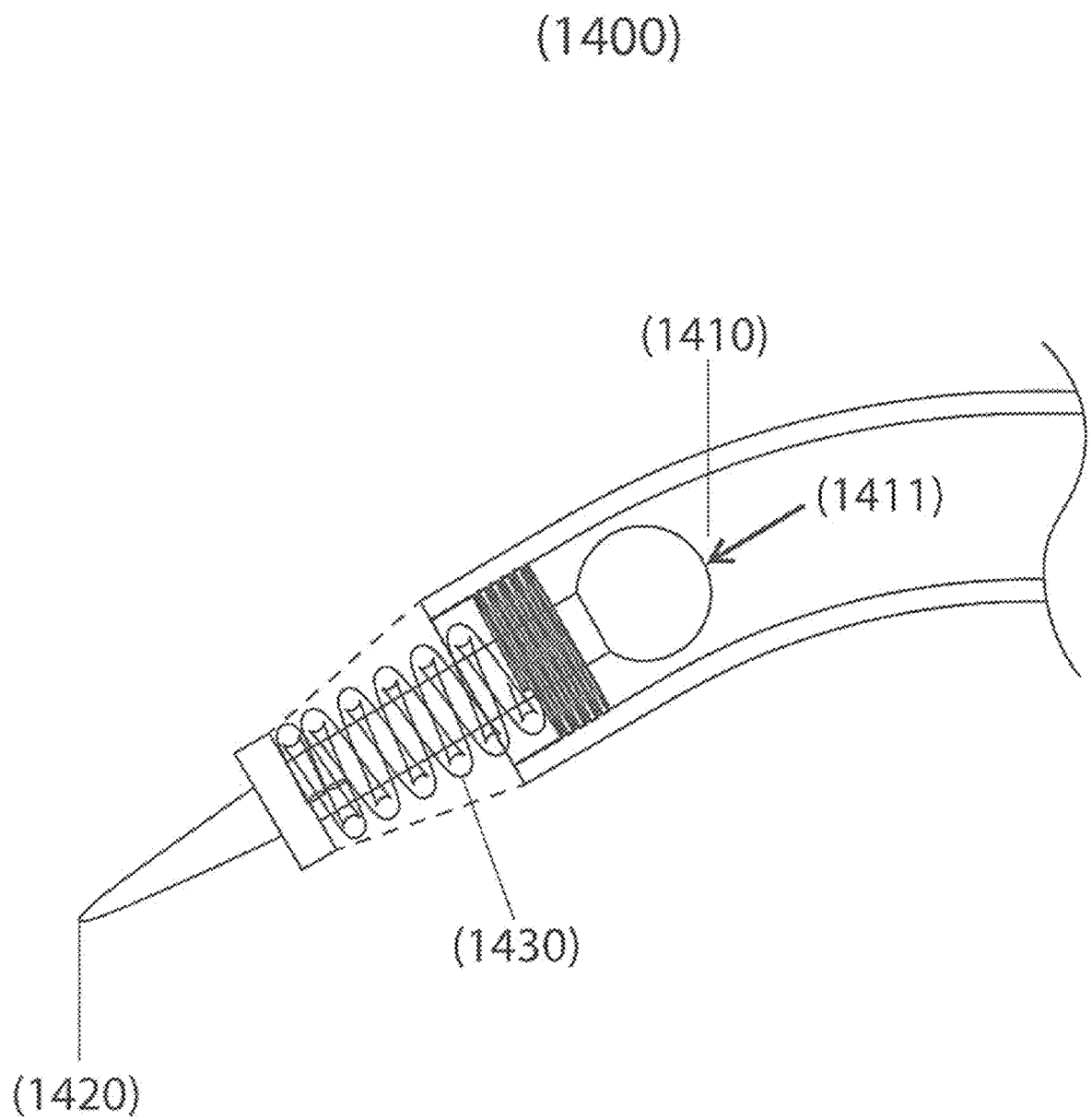
FIG. 14 is an assembled view of one possible embodiment of the Tip (1400).
Figure 15:
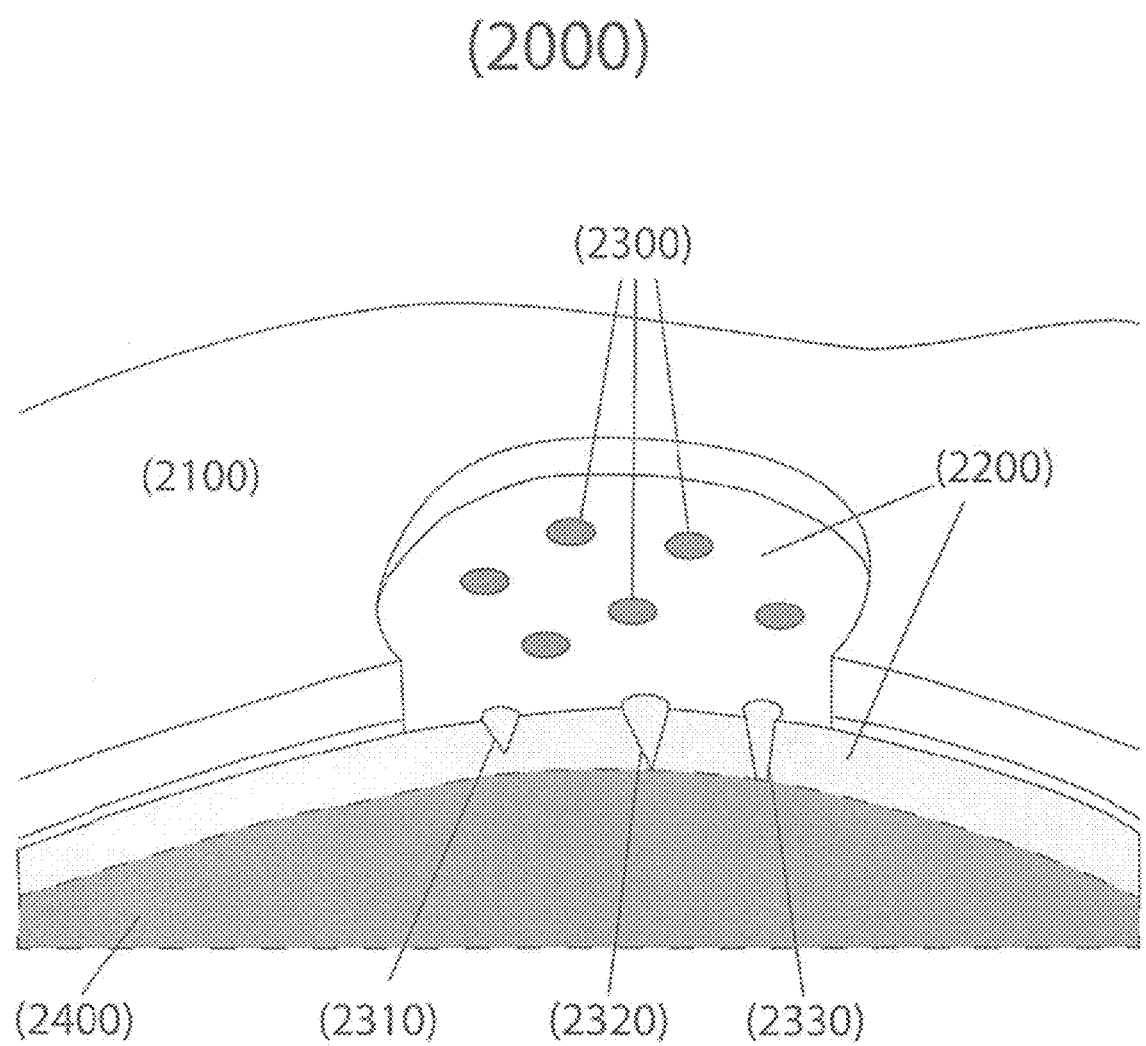
FIG. 15 illustrates a variety of different holes that could be created by a microfracture procedure.
Figure 16:
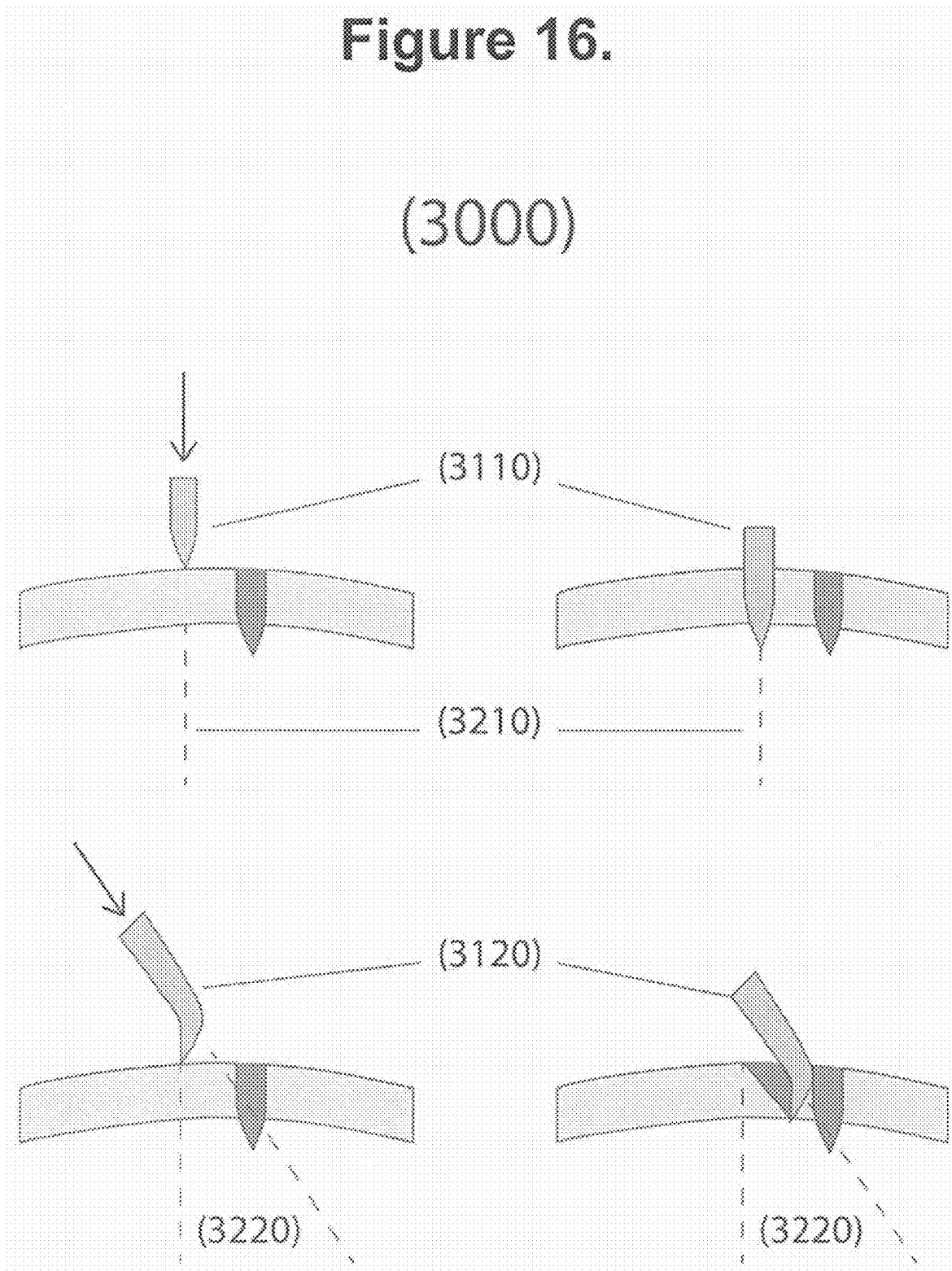
FIG. 16 illustrates the effect of 'skiving' in microfracture due to the misalignment of the tip, the force vector, and the subchondral bone plate (3000).
Figure 17:
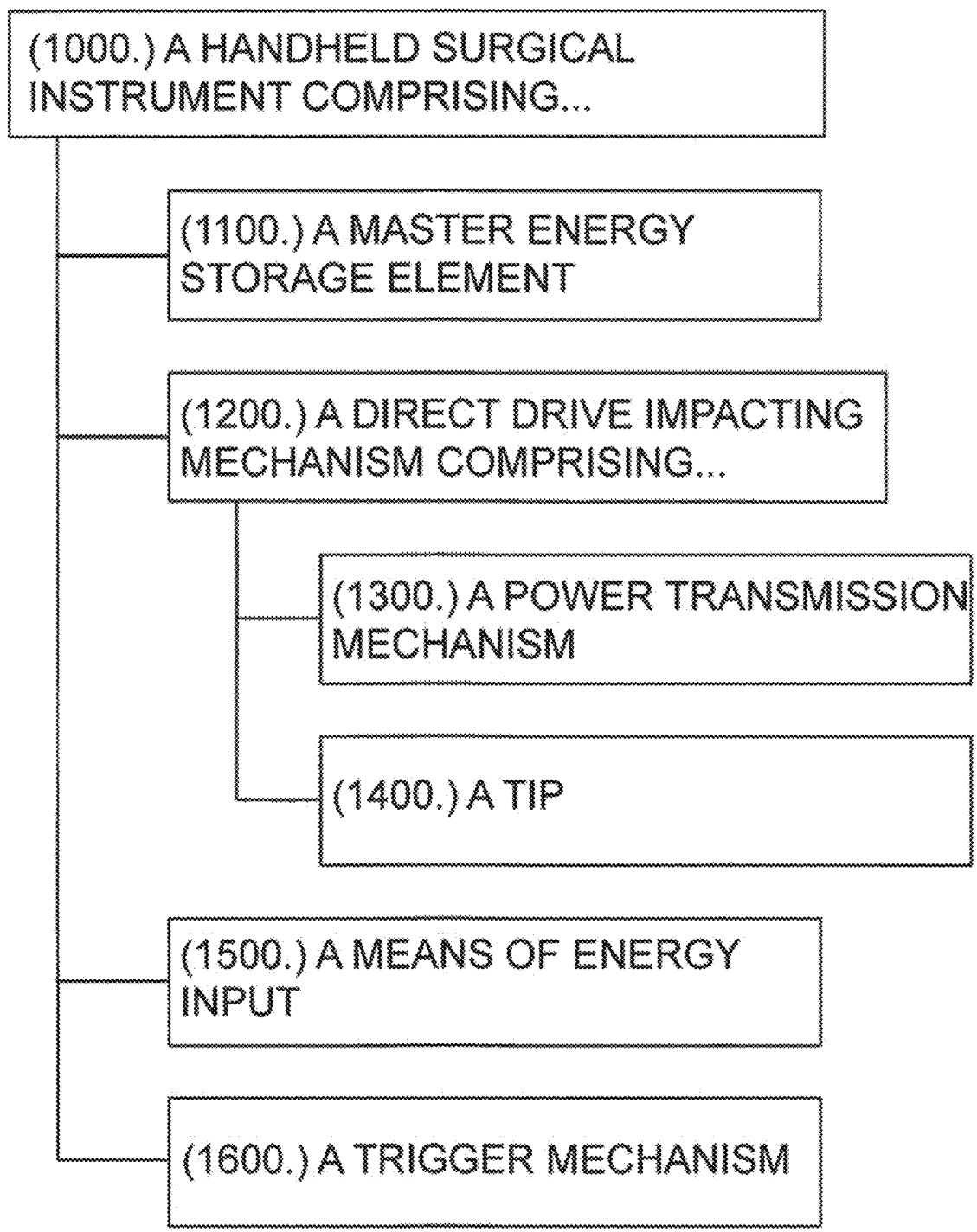
FIG. 17 is a block diagram of the Device (1000) in one embodiment.
Figure 21:
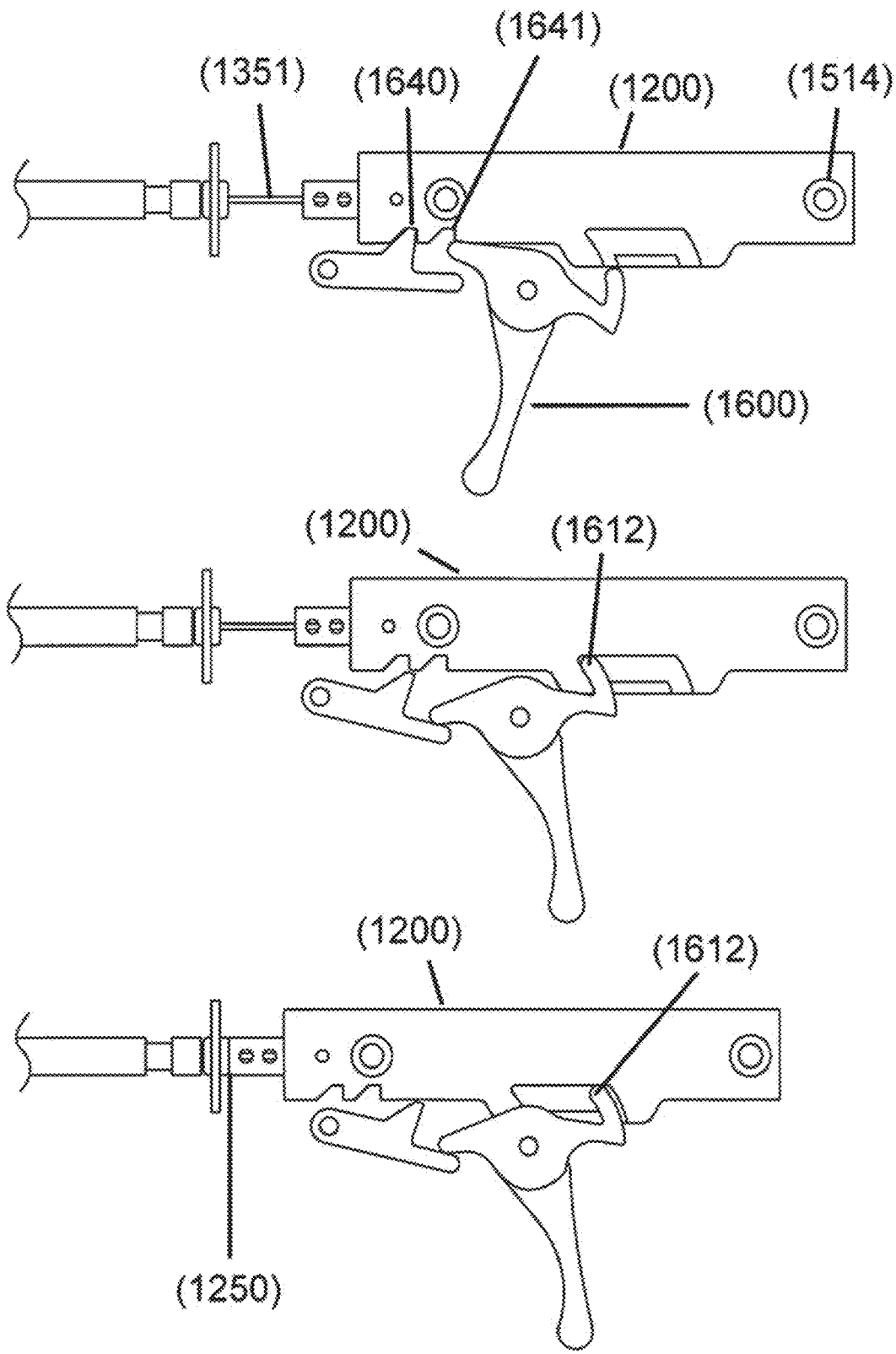
FIG. 21 illustrates an example Trigger Mechanism (1600) embodiment and its interface with the Power Transmission Mechanism (1300).
Figure 22:
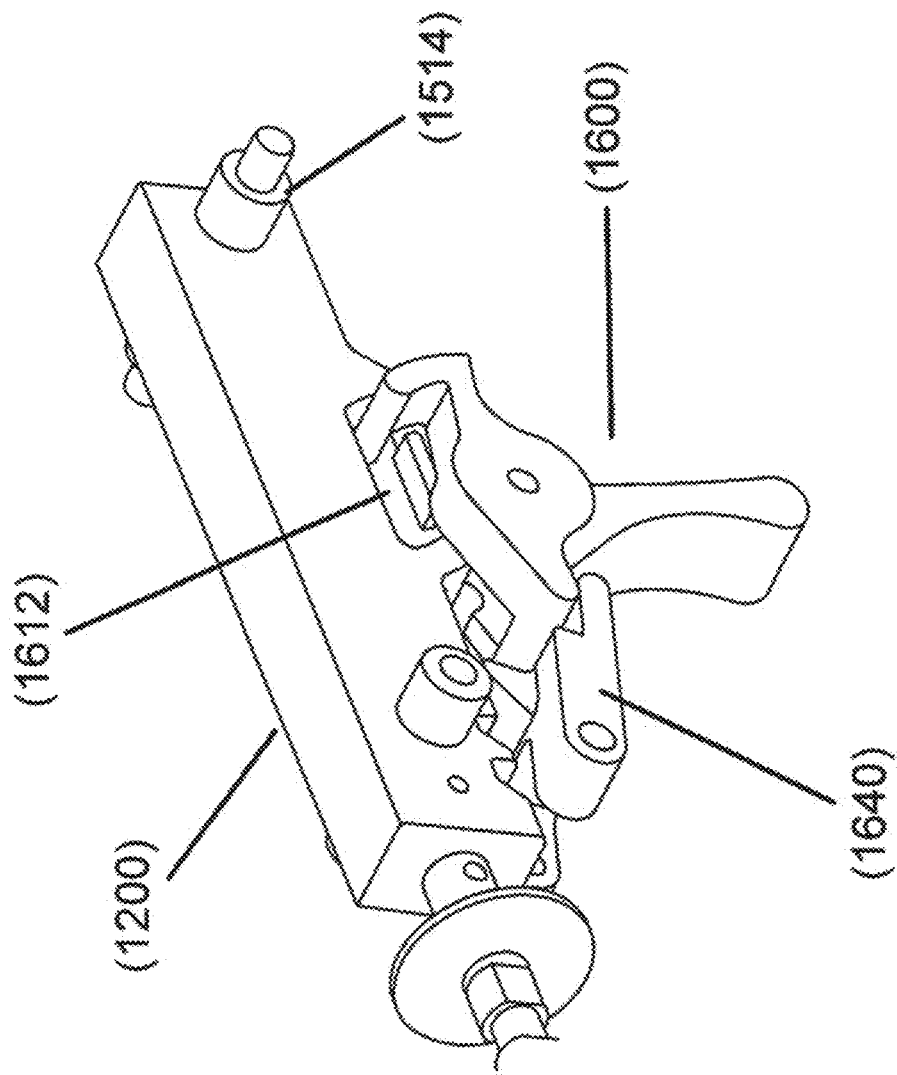
FIG. 22 is an orthographic view of one possible Trigger Mechanism (1600) embodiment.
Figure 24:
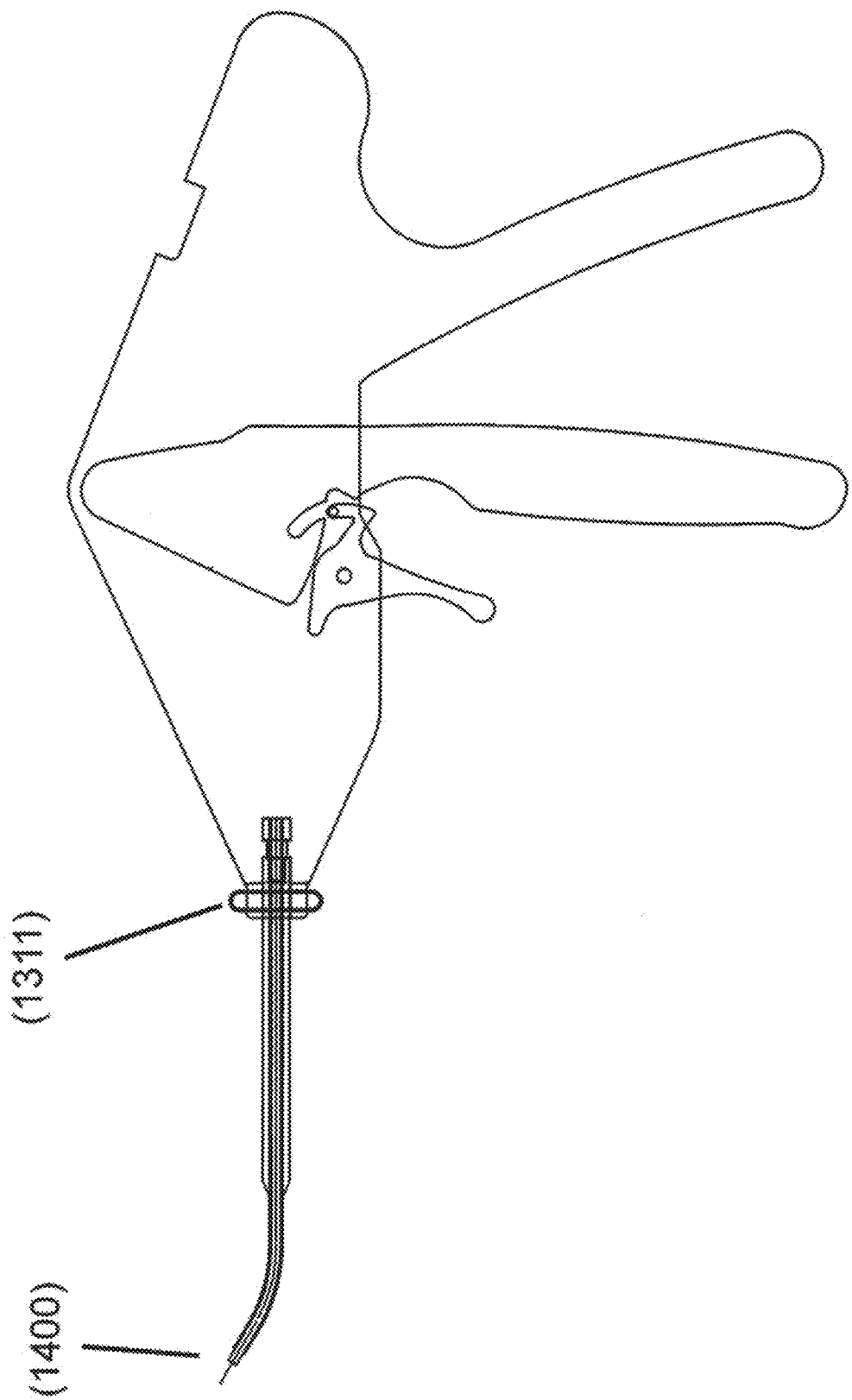
FIG. 24 illustrates an alternative or dynamic orientation of the shaft, transmission mechanism and tip.
Figure 26:
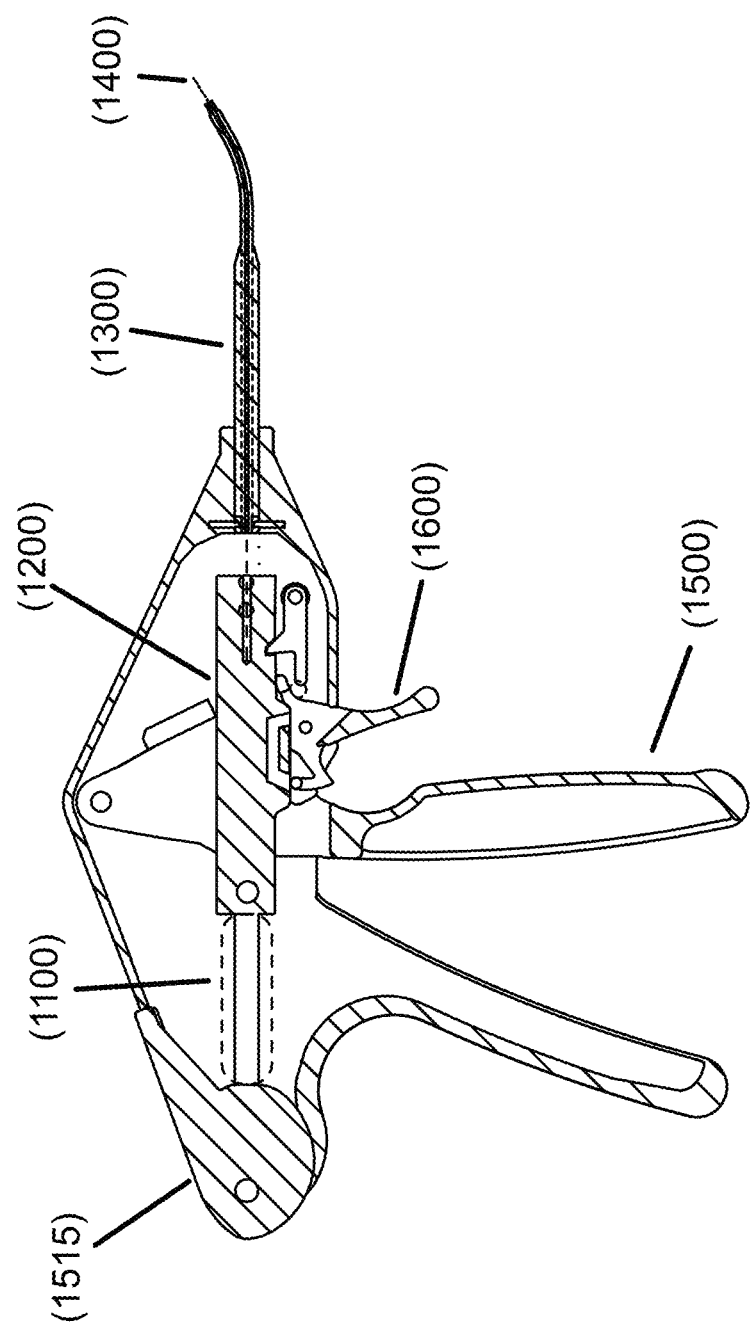
FIG. 26 illustrates a cross-sectional view of one embodiment of the Device.
Figure 28:
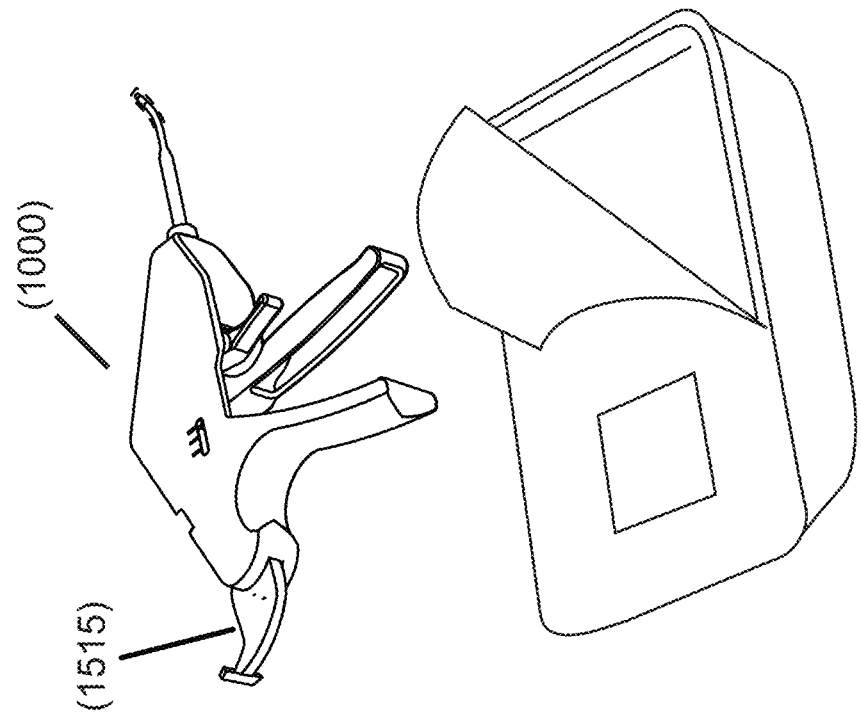
FIG. 28 illustrates an example embodiment of the Device in fully disposable form.
Figure 27:
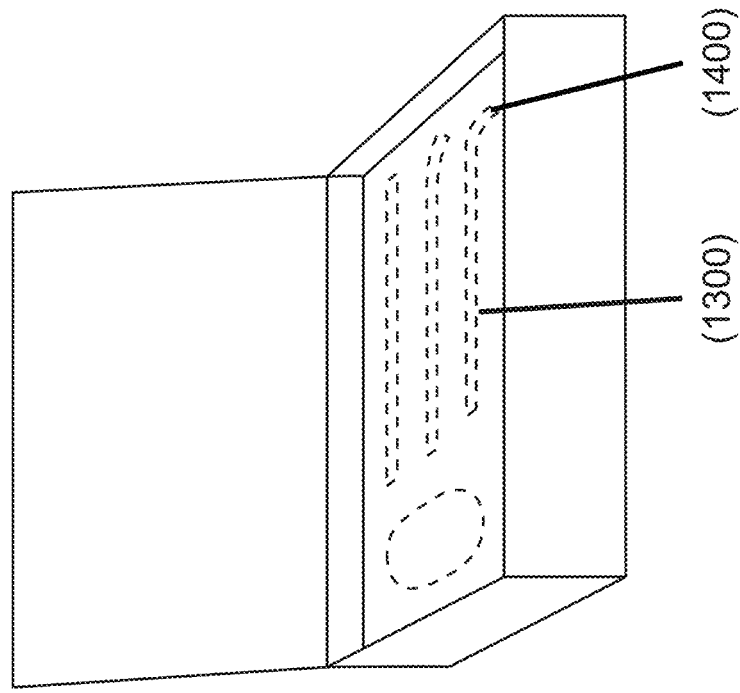
FIG. 27 illustrates an example kit in which a plurality of Transmission Mechanisms and Tips of varying geometry are provided.

In one embodiment, the device exists as an attachment which can combine with existing tools as a means of providing an energy input, a handle, and/or a trigger. FIG. 8 illustrates one possibility of how the block diagram in FIG. 1 could be "short-circuited" or plugged into another device.

In another embodiment, the Means of Energy Input is a lever attached to the handle. Operating this lever could progressively charge the Energy Storage Element. The Impact Mechanism could optionally be triggered once the charge lever reaches a predetermined position. The Impact Mechanism could optionally be triggered by the user at any position, giving the user added control in the amount of force transmitted by the Impact Mechanism. The charge lever could optionally include a ratcheting mechanism for multiple operations by the user before triggering.

The master energy storage element (1100) enables the device to store sufficient energy to match the requirement for the creation of two or more holes. The master energy storage element may include some means of engagement (1170) with the power transmission (1300) and/or the impact mechanism. The master energy storage element may exist, by way of example and not limitation, in one of the following forms; a compressed fluid chamber (1110); a chemically-based battery (1120); a mechanical flywheel (1130); a hydraulic reservoir (1140); a flat spring (1150); a linear spring (1160).

The impact mechanism provides a means by which to apply a force to ultimately be transmitted to the tip for the creation of one or more holes. The impact mechanism may be charged (1210) by the master energy storage element (1100); and may also utilize a mechanism for the reduction of recoil (1220) on the user. The impact mechanism is optionally driven by a secondary energy storage element (1230). In one embodiment, the impact mechanism is driven directly by the master energy storage element (1240). In one embodiment, the impact mechanism provides a force to the power transmission mechanism (1300). In one embodiment, the device includes a damper (1250) to soften the residual impact delivered by the impact mechanism.

The power transmission mechanism (1300) receives energy input from the impact mechanism (1320) or the master energy storage element; and provides a means by which to transmit power and provide output energy to the tip (1330); optionally utilizing one or more springs as a buffer or for position restoration (1340). The power transmission mechanism optionally transfers the direction of force (1310) applied by the impact mechanism. In one embodiment, the power transmission mechanism transfers the direction of force by 30 degrees. In another embodiment, the power transmission mechanism transfers the direction of force by 90 degrees. The power transmission mechanism is optionally enclosed in a flexible or bendable housing, and constructed in such a manner to allow for corresponding freedom of form (1350). The power transmission mechanism optionally utilizes one or more spherical bodies within a smooth, constrained pathway for the facilitation of efficient energy transfer (1360).

The tip (1400) optionally exists as an assembly comprising of one or more springs (1430) to provide a buffer between attached bodies or for repositioning and comprises a proximal end (1410), which may be engaged by the power transmission mechanism; and a distal end (1420), optionally with a sharpened point (1421); optionally comprising one or more wires (1422); optionally with a chisel or drill-like geometry (1423); optionally comprising a multitude of impact points (1424). The tip optionally has a diameter of 1 millimeter or less in order to limit excessive damage to the subchondral bone, while still providing the necessary blood flow access for cartilage regeneration.

The means of energy input (1500) allows a user to add energy to the devices energy storage elements for the subsequent utilization of internal mechanisms. The means of energy input is optionally hand operated (1510); the means of energy input is optionally performed utilizing non-human external assistance (1520).

If by manual user operation, in one embodiment, the means of energy input is detachable (1511). In another embodiment, the means of energy input is a rotatable crank lever (1512). In one embodiment, the means of energy input is a sliding handle (1513).

If by way of non-human external assistance, the means of energy input could be in the form of fluid power (1521) or an electromechanical system (1522).

The trigger mechanism (1600) provides a way to initiate mechanisms for the subsequent creation of holes in tissue and may interact with any other part in the device (1000) such as the impact mechanism (1640) or the master energy storage element (1650). The interface between the impact mechanism and the trigger mechanism optionally includes multiple detents (1641) to enable a ratcheting effect during energy input. The trigger mechanism optionally comprises of one or more safety locking mechanisms (1610) and is optionally a double set trigger, or optionally a progressive or staged trigger (1630). One embodiment of the safety mechanism is a pin (1611) that, when displaced in a particular direction, interferes with the firing operation of the trigger. Another embodiment of a safety mechanism is a separate track and body (1612) which together only allow firing of the trigger when the device is in a particular state.

In one embodiment of the device, the impact mechanism, the transmission mechanism, and the tip are all connected to each other so as to accelerate the tip directly, without relying primarily on impact proximally within the device. In this embodiment, the transmission mechanism may exist as a semi-flexible element (1351) such as a steel, nitinol, or titanium wire, which can traverse a bend in the shaft (1352) without failure. The drive carriage may be charged, triggered, and fired using a spring (1160) capable of storing enough energy to penetrate dense human tissue or bone. The drive carriage may be partially or fully decoupled from the handle body at the moment of impact by allowing the spring to accelerate the impact carriage and tip before impacting the tissue; Such configuration reduces device kick-back in the direction of the operator on impact. Additionally, the handle body may include added weight for increased inertia and resulting decreased acceleration in the direction of the operator. The energy storage element (1100) may transfer energy for part of, or most of, the stroke of the direct drive carriage so as to reduce recoil or kick-back on the operator. It has been discovered that, with a sharpened surgical stainless steel tip of 1.0 mm diameter, a kinetic energy of greater than 0.7 joules at the moment of impact results in sufficient depth of penetration (6-8 mm) in 30# bone foam substrate, which closely resembles subchondral bone plate. In one embodiment, the direct drive carriage is attached to a bundle of wires that make up the tip or several tips for simultaneous or sequential impact.

Device may include a feature enabling the impacting tip (1400) to retract, or move proximally relative to the shaft, utilizing sufficient leverage to pull the tip out of the tissue after impacting. This leverage may be applied with one or more of the following, including but not limited to a screw, a cam, a roller, a slider crank, a pull wire, or some combination thereof. FIG. 18 shows one example of this utilizing a cam and a roller (1514). In one embodiment, this leverage is applied using the same hand that triggers the impact by way of a lever. In one embodiment, this leverage is applied using a second hand. In one embodiment, this mechanism is assisted by a spring. Retraction mechanism optionally utilizes a ratcheting or indexing mechanism, preventing premature triggering and/or enabling the user to operate retraction lever more than once so that sufficient mechanical advantage and stroke are attainable.

Device may include an element enabling the visualization of impact positioning before triggering impact. In one embodiment, this feature exists as a stop point in the stroke of the tip (1425), such as that enabled by a locking pawl. In doing so, the operator may do a portion of, or a majority of drive carriage charging before placing in position, reducing the stability disturbance and alignment challenge while charging, and also exhibiting precise placement of the impacting tip. In one embodiment, the visualization element exists as a separate body from the impacting tip. In this embodiment, the visualization element could attach to the primary drive wire by means of element including but not limited to a wire, a spring, a channel or other body. In one embodiment, the visualization element is a laser. In one embodiment, the visualization element is a focused stream of fluid.

Device optionally features a depth indicator on the handle body or shaft to show relative or absolute depth of penetration into the tissue. In one embodiment, this indicator exists as a marker on the drive carriage (1201), viewable through an opening in the side of the handle body, for which the distance from the marker to the end of the tip is constant at the moment after impact. This depth indicator optionally features a finite set of two or more result indicators (1202), for example and not limitation, a binary indicator to indicate sufficient depth or not sufficient depth, or a scaled indicator to indicate what range or percentile of depth penetration was achieved. This feature is optionally embodied by an infinite relative position indicator window which may or may not have guiding markings on it. In one embodiment, the markings on the indicator depict a typical range of thicknesses of cortical bone, to assist the operator in conceptualizing the resulting impact depth.

The device may be assembled, packaged, and shipped with the main energy storage element completely uncharged, or partially uncharged. In such an embodiment, the user may prime the device when it is ready for use by introducing initial single operation energy input. In doing so at this stage as opposed to upon assembly of the device and before storage of the device reduces possibility of creep, wear, and deformation. The act of priming the device may also serve as a means to communicate to the user that the device is now ready for use and should be handled as such. In one embodiment, the means of delivering initial energy input to prime the device is a rotational cam (1515) that interfaces with one end of a spring. A leveraging element for priming may be attached to or shipped with the device.

The semi-flexible drive element and/or the shaft may be produced or processed in such a way to yield an interface or multiple interfaces with low coefficients of friction. This may be done with a smooth or lubricious coating such as a PTFE or EPTFE or biocompatible lubricant. This may be achieved with a metal impregnated with a biocompatible lubricant. This may be achieved with a surface treatment to bare wire such as polishing, plating or lapping. Internal friction may be reduced by reducing the total surface area in contact between the inside of the shaft and the outside of the drive element, such as one or more surrounding collars applying the pressure instead of solely the inner wall of the cannula or shaft applying pressure.

The shaft or cannula may feature a non-uniform axial profile (1441) in order to optimize one or more of the following: stiffness, accessibility, control, and/or visualization. In one embodiment, this is done with two or more nested tubes of different diameters, optionally welded for rigidity.

In one embodiment, this is done with a single shaft, stepped and/or gradually tapered down its length. In one embodiment, the distal tip of the shaft or cannula has a sharp edge (1442), whether straight, jagged, segmented or otherwise. This sharp edge could be on the interior diameter, outer diameter, or both.

The device optionally includes a mechanism (1311) allowing the shaft or cannula to rotate on its primary axis, improving control and ergonomic functionality by modifying the direction of impact relative to the operator's hand. In one embodiment, this mechanism exists as two or more finite positions of angular displacement. In one embodiment, this mechanism exists as a joint of infinite angular positioning. In one embodiment, this articulation can be actively controlled with the same hand that holds the device. In one embodiment, this articulation is performed using a second hand. The device may be made available with several different tip angles, optionally packaged and sold together in a kit. The device may be packaged and sold with a tool and or instruction for the operator to bend the tip before use to their desired position.

The foregoing description of the example embodiments has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather determined by the claims appended hereto.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the mechanical, electro-mechanical, and electrical arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

The invention claimed is:

1. A method for impacting a body part with a surgical device, the surgical device including an energy storage element coupled to an impacting mechanism, wherein the impacting mechanism includes a wire with a tip configured to impact a bone;

A power transmission mechanism configured to transmit energy from the energy storage element to the impacting mechanism, wherein the wire is guided by a hollow shaft, wherein the hollow shaft includes a bend in a distal end; and A trigger mechanism configured to release energy from the energy storage element, wherein the trigger mechanism further includes a locking mechanism configured to lock the energy storage mechanism in a safe position; and a handle and a lever combination, wherein the handle is in a fixed position and the lever is capable of rotation towards the handle which retracts the tip and charges the energy storage element;

the method comprising;

Directing the impacting mechanism to the body part, said impacting mechanism coupled to the surgical device;

Activating the power transmission mechanism coupled to the impacting mechanism, said power transmission mechanism to generate a force sufficient to impact the body part; and Advancing the impacting mechanism to impact the body part, said advancing initiated by a controller.

2. The method of claim 1 further including retracting the impacting mechanism.

3. The method of claim 1 wherein the energy storage element may include a compressed air source, a battery, a flywheel, or a spring.

4. The method of claim 1 wherein the surgical device is a hand held surgical device.

5. The method of claim 1 wherein the impacting mechanism includes a rigid body terminating in a tip.

6. The method of claim 5 wherein the rigid body includes an internal channel extending through the tip.

7. The method of claim 6 wherein the internal channel is operably coupled to a reservoir for collecting or inserting material through the channel to or from the body part.

8. The method of claim 1 further including retracting the impact mechanism and simultaneously charging the power transmission mechanism.

9. The method of claim 1 wherein the controller includes a locking mechanism to prevent unexpected advancing of the impact mechanism.

10. A method for impacting a body part with a surgical device, the surgical device including an energy storage element coupled to an impacting mechanism, wherein the impacting mechanism includes a wire with a tip configured to impact a bone;

a power transmission mechanism configured to transmit energy from the energy storage element to the impacting mechanism, wherein the wire is guided by a hollow shaft, wherein the hollow shaft includes a bend in a distal end; and a trigger mechanism configured to release energy from the energy storage element, wherein the trigger mechanism further includes a locking mechanism configured to lock the energy storage mechanism in a safe position; and a handle and a lever combination, wherein the handle is in a fixed position and the lever is capable of rotation towards the handle which retracts the tip and charges the energy storage element;

the method comprising;

Charging the energy storage element operably connected to the surgical device;

Aligning the impacting mechanism of the surgical device with the body part of interest;

Activating the power transmission mechanism operably connected to the energy storage element, said power transmission mechanism providing sufficient power to advance the impacting mechanism;

Retracting the impacting mechanism while simultaneously charging the energy storage element.

11. A method for delivering an impact to a body part, the impact provided by a surgical device, the surgical device including an energy storage element coupled to an impacting mechanism, wherein the impacting mechanism includes a wire with a tip configured to impact a bone;

A power transmission mechanism configured to transmit energy from the energy storage element to the impacting mechanism, wherein the wire is guided by a hollow shaft, wherein the hollow shaft includes a bend in a distal end; and A trigger mechanism configured to release energy from the energy storage element, wherein the trigger mechanism further includes a locking mechanism configured to lock the energy storage mechanism in a safe position; and a handle and a lever combination, wherein the handle is in a fixed position and the lever is capable of rotation towards the handle which retracts the tip and charges the energy storage element;

the method comprising;

Aligning the impacting mechanism of the surgical device to provide an impact with the body part of interest;

Triggering the power transmission mechanism operably connected to the impacting mechanism to advance the impacting mechanism;

Delivering the impacting mechanism into the body part;

Retracting the impacting mechanism from the body part;

Wherein the impacting mechanism includes a guide shaft and an impacting tip disposed for travel through the guide shaft.

12. The method of claim 11 further including repeating the steps of delivering the impact mechanism and retracting the impacting mechanism using the same surgical device.

13. The method of claim 11 wherein the energy storage element may include a compressed air source, a battery, a flywheel, or a spring, said energy storage unit is independent of the surgical device.

14. The method of claim 11 wherein the surgical device is a hand held surgical device.

15. The method of claim 11 wherein the retracting step is performed by activating a lever attached to the surgical device.

16. The method of claim 11 wherein impacting mechanism includes an internal channel extending through the tip.

17. The method of claim 16 wherein the internal channel is operably coupled to a reservoir for collecting or inserting material through the channel to or from the body part.

18. The method of claim 11 further including retracting the impacting mechanism and simultaneously charging the power transmission mechanism.

* * * * *